(12) United States Patent
Tripp et al.

(10) Patent No.: US 8,815,306 B2
(45) Date of Patent: *Aug. 26, 2014

(54) METHODS AND COMPOSITIONS FOR PROMOTING BONE AND JOINT HEALTH

(75) Inventors: Matthew L. Tripp, Gig Harbor, WA (US); Veera Konda, Gig Harbor, WA (US); Anu Desai, Gig Harbor, WA (US); Amy J. Hall, Gig Harbor, WA (US); Jeffrey S. Bland, Fox Island, WA (US)

(73) Assignee: Metaproteomics, LLC, San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/048,613

(22) Filed: Mar. 14, 2008

(65) Prior Publication Data

US 2008/0242690 A1 Oct. 2, 2008

Related U.S. Application Data

(60) Provisional application No. 60/918,727, filed on Mar. 19, 2007.

(51) Int. Cl.
*A61K 36/00* (2006.01)
*A61K 31/4353* (2006.01)
*A61K 31/122* (2006.01)

(52) U.S. Cl.
USPC ............................. 424/725; 514/280; 514/690

(58) Field of Classification Search
None
See application file for complete search history.

(56) References Cited

U.S. PATENT DOCUMENTS

| | | |
|---|---|---|
| 3,451,821 A | 6/1969 | Todd et al. |
| 3,552,975 A | 1/1971 | Worden et al. |
| 3,720,517 A | 3/1973 | Bavisotto et al. |
| 3,932,603 A | 1/1976 | Haas |
| 3,933,919 A | 1/1976 | Wilkinson |
| 3,965,188 A | 6/1976 | Westermann et al. |
| 4,123,561 A | 10/1978 | Grant |
| 4,133,903 A | 1/1979 | Thiele et al. |
| 4,148,873 A | 4/1979 | Owades |
| 4,154,865 A | 5/1979 | Grant |
| 4,170,638 A | 10/1979 | Owades |
| 4,389,421 A | 6/1983 | Palamand |
| 4,401,684 A | 8/1983 | Versluys |
| 4,473,551 A | 9/1984 | Schinitsky |
| 4,554,170 A | 11/1985 | Panzner et al. |
| 4,644,084 A | 2/1987 | Cowles et al. |
| 4,692,280 A | 9/1987 | Spinelli |
| 4,767,640 A | 8/1988 | Goldstein et al. |
| 4,857,554 A | 8/1989 | Kallimanis |
| 5,006,337 A | 4/1991 | Motitschke et al. |
| 5,013,571 A | 5/1991 | Hay |
| 5,041,300 A | 8/1991 | Todd et al. |
| 5,073,396 A | 12/1991 | Todd et al. |
| 5,082,975 A | 1/1992 | Todd et al. |
| 5,155,276 A | 10/1992 | Paul |
| 5,166,449 A | 11/1992 | Todd et al. |
| 5,264,236 A | 11/1993 | Ogasahara et al. |
| 5,286,506 A | 2/1994 | Millis et al. |
| 5,296,637 A | 3/1994 | Stegink et al. |
| 5,370,863 A | 12/1994 | Barney et al. |
| 5,387,425 A | 2/1995 | Hsu et al. |
| 5,604,263 A | 2/1997 | Tobe et al. |
| 5,641,517 A | 6/1997 | Eskeland et al. |
| 5,827,895 A | 10/1998 | Nutter et al. |
| 5,919,813 A | 7/1999 | De Juan |
| 5,968,539 A | 10/1999 | Beerse et al. |
| 6,020,019 A | 2/2000 | Ting et al. |
| 6,129,907 A | 10/2000 | Sreenivasan et al. |
| 6,200,594 B1 | 3/2001 | Ernest et al. |
| 6,224,871 B1 | 5/2001 | Hastings et al. |
| 6,264,995 B1 | 7/2001 | Newmark et al. |
| 6,291,483 B1 | 9/2001 | Upadhyay et al. |
| 6,383,527 B1 | 5/2002 | Artman et al. |
| 6,391,346 B1 | 5/2002 | Newmark et al. |
| 6,440,465 B1 | 8/2002 | Meisner |
| 6,447,762 B1 | 9/2002 | Casadó Galcerá |
| 6,482,456 B1 | 11/2002 | Yokoo et al. |
| 6,583,322 B1 | 6/2003 | Shalai et al. |
| 6,689,388 B2 | 2/2004 | Kuhrts |
| 6,790,459 B1 | 9/2004 | Cheng et al. |
| 6,801,860 B1 | 10/2004 | Dessen et al. |
| 7,195,785 B2 | 3/2007 | Babish et al. |
| 7,205,151 B2 | 4/2007 | Babish et al. |
| 7,270,835 B2 | 9/2007 | Tripp et al. |
| 7,279,185 B2 | 10/2007 | Babish et al. |
| 7,332,185 B2 | 2/2008 | Babish et al. |
| 7,431,948 B2 | 10/2008 | Tripp et al. |
| 2002/0028852 A1 | 3/2002 | Ghai et al. |
| 2002/0076452 A1 | 6/2002 | Babish et al. |

(Continued)

FOREIGN PATENT DOCUMENTS

| | | |
|---|---|---|
| DE | 2212148 | 9/1972 |
| DE | 3931147 | 3/1991 |

(Continued)

OTHER PUBLICATIONS

International Search Report for corresponding PCT Application No. PCT/US08/56980, 2 pp, (2008).
Written Opinion for corresponding PCT Application No. PCT/US08/56980, 4 pp, (2008).
Van der Kraan, et al., Anabolic and Destructive Mediators in Osteoarthritis, Curr Opin Nutr Metab Care 3:205-211, 2000.
Iannone, et al., The Pathophysiology of Osteoarthritis, Aging Clin Exp Res. 15:364-372, 2003.
Dieppe, et al., Pathogenesis and Management of Pain in Osteoarthritis. Lancet. 365:965-73;2005.

(Continued)

*Primary Examiner* — Bong-Sook Baek
(74) *Attorney, Agent, or Firm* — McDermott Will & Emery LLP

(57) ABSTRACT

Methods and compositions that can be used to promote bone and joint health through amelioration, stabilization and repair of damage associated with various pathophysiological conditions are disclosed.

10 Claims, 1 Drawing Sheet

(56) References Cited

U.S. PATENT DOCUMENTS

| | | |
|---|---|---|
| 2002/0077299 A1 | 6/2002 | Babish et al. |
| 2002/0086062 A1 | 7/2002 | Kuhrts |
| 2002/0086070 A1 | 7/2002 | Kuhrts |
| 2002/0156087 A1 | 10/2002 | Nuss et al. |
| 2003/0008021 A1 | 1/2003 | Babish et al. |
| 2003/0077313 A1 | 4/2003 | Schwartz et al. |
| 2003/0096027 A1 | 5/2003 | Babish et al. |
| 2003/0113393 A1 | 6/2003 | Babish et al. |
| 2003/0133958 A1 | 7/2003 | Kuno et al. |
| 2003/0180402 A1 | 9/2003 | Jia et al. |
| 2004/0072900 A1 | 4/2004 | Artman et al. |
| 2004/0086580 A1 | 5/2004 | Tripp et al. |
| 2004/0115290 A1 | 6/2004 | Tripp et al. |
| 2004/0137096 A1 | 7/2004 | Kuhrts |
| 2004/0151792 A1 | 8/2004 | Tripp et al. |
| 2004/0219240 A1 | 11/2004 | Babish et al. |
| 2005/0042317 A1 | 2/2005 | Babish et al. |
| 2005/0129791 A1 | 6/2005 | Babish et al. |
| 2005/0191375 A1 | 9/2005 | Babish et al. |
| 2005/0192356 A1 | 9/2005 | Babish et al. |
| 2006/0127511 A1 | 6/2006 | Tripp et al. |
| 2006/0127512 A1 | 6/2006 | Tripp et al. |
| 2006/0127513 A1 | 6/2006 | Tripp et al. |
| 2006/0127514 A1 | 6/2006 | Tripp et al. |
| 2006/0127515 A1 | 6/2006 | Tripp et al. |
| 2006/0127516 A1 | 6/2006 | Tripp et al. |
| 2006/0127517 A1 | 6/2006 | Tripp et al. |
| 2006/0193933 A1 | 8/2006 | Tripp et al. |
| 2006/0269627 A1 | 11/2006 | Jia et al. |
| 2007/0020352 A1 | 1/2007 | Tripp et al. |
| 2007/0160692 A1 | 7/2007 | Tripp et al. |
| 2007/0166418 A1 | 7/2007 | Tripp et al. |
| 2007/0172532 A1 | 7/2007 | Babish et al. |
| 2007/0184133 A1 | 8/2007 | Tripp et al. |
| 2009/0118373 A1 | 5/2009 | Tripp et al. |

FOREIGN PATENT DOCUMENTS

| | | |
|---|---|---|
| DE | 19841615 | 3/2000 |
| EP | 0606599 A1 | 7/1994 |
| EP | 0681029 A2 | 11/1995 |
| EP | 2626077 A2 | 8/2013 |
| GB | 2330076 | 4/1999 |
| JP | 363211219 | 9/1988 |
| JP | 04202138 | 7/1992 |
| JP | 6312924 | 11/1994 |
| JP | 07194351 | 8/1995 |
| JP | 8073369 | 3/1996 |
| JP | 9067245 | 3/1997 |
| JP | 410025247 | 1/1998 |
| JP | 10152428 | 6/1998 |
| RU | 2045955 | 10/1995 |
| SU | 1247011 | 7/1986 |
| WO | WO99/44623 | 9/1999 |
| WO | WO00/68356 | 11/2000 |
| WO | WO00/74696 | 12/2000 |
| WO | WO02/02582 | 1/2002 |
| WO | WO03/082249 | 10/2003 |

OTHER PUBLICATIONS

Doan T, et al. Rheumatoid Arthritis: An Overview of New and Emerging Therapies. J Clin Pharmacol. 45:751-62; 2005.
Bingham III. The Pathogenesis of rheumatoid arthritis: Pivotal cytokines involved in bone degradation and inflammation. J Rheumatol. 29 (suppl 65).3-9; 2002.
Bone Health and Osteoporosis: A Report of the Surgeon General, U.S. Department of Health and Human Services, 2004.
Felson et al, Osteoarthritis: New insights, Ann Intern Med. 133:635-46;2000.
Goldring, The Role of the Chondrocyte in Osteoarthritis, Arthritis Rheum. 43:1916-26;2000.
Hinton, et al., Osteoarthritis: Diagnosis and Therapeutic Considerations, Amer Fam. Physician, 65:841-848, 2002.
Ivanovska, et al., Study on the Anti-Inflammatory Action of Berberis Vulgaris Root Extract, Alkaloid Fractions and Pure Alkaloids, Int. J. Immunopharmac. 18:553-561, 1996.
Lawrence, et al., Estimates of the Prevalence of Arthritis and Selected Musculoskeletal Disorders in the United States, Arthritis & Rheumatims, 41:778-799, 1998.
Lee, et al., Rheumatoid Arthritis, The Lancet, 358:903-911, 2001.
Leng, et al., Therapeutic Effects of Berberine in Impaired Glucose Tolerance Rats and Its Influence on Insulin Secretion, Acta Pharmacol Sin, 25:496-502, 2004.
Mekawi, Effect of Berberine Alkaloid on Cholera Vibrio and its Endotoxin, J Egypt Med Assoc. 49(8):554-9, 1966.
Mohan, M., et al., "Berberine in trachoma. (A clinical trial)." Indian J Ophthalmol. 30(2):69-75, 1982.
Pelletier, Osteoarthritis, an Inflammatory Disease Potential Implication for the Selection of New Therapeutic Targets, Arthritis Rheum. 44:1237-1247;2001.
Rindfleisch JA, Muller D. "Diagnosis and Management of Rheumatoid Arthritis," Am Fam Physician. 72:1049-50; 2005.
Sabir, M., et al., "Experimental Study of the Antitrachoma Action of Berberine", Indian J Med Res. 64(8):1160-1167, 1976.
"Information on arthrotrimtm product", downloaded from Internet Aug. 30, 2002.
"Information on Zyflamend and Zyflamend PM", downloaded from Internet Aug. 30, 2002.
Albal, MV., et al., "Clinical evaluation of berberine in mycotic infections." Indian J. Ophthalmol 34:91-2 (1986).
Anto, et al. Pharm. Pharmacol. Comm. 4:103-106 (1998).
Bermejo, et al. Rev. Esp. Enferm. Dig. 95: 621-624 and 625-628 (2003).
Bmj, Donovan et al., 3 pages (1999) 318:299-300 (Jan. 30).
Brown, et al. J. Chem. Soc. 545 (1959).
Byrne, et al. J. Chem. Soc. (c):2810 (1971).
Carroccio, et al. Clin. Chem. 49:861-867 (2003).
Carson, J., Am. Chem. Soc. 73:1850-1851 (1951).
Chandra, et al. Indian J. Medical Research 60(1):138-142 (1972).
Charlier, et al. Eur. J. Med. Chem. 38:645-659 (2003).
Chou et al. Eur. J. Biochem. 115:207-216 (1981).
Chou, et al. Adv enzyme regul 22:27-55 (1984).
Chou, et al. J. Biol. Chem. 252:6438-6442 (1977).
Chou, et al. J. Theor. Biol. 35:285-297 (1972).
Chou, et al. Trends Pharm. Sci. 4:450-454 (1983).
Chou, j. Theor. Biol. 59:253-276 (1976).
Cohen, Protein Kinases—the major drug targets of the twenty-first century? Nature Reviews, 1: 309-315 (2002).
Costa, et al. Digest. Liver Dis. 35:642-647 (2003).
Davies, WL. Abstract—Fertiliser, Feeding stuffs and Farm Supplies J. 11:694 (1926).
Ding, et al. Biochem. Biophy. Res. Comm. 261:218-223 (1999).
Friedman, et al. J Cutan Med. Surg. 6(5):449-459 (2002).
Gerhauser, Beer Constituents as Potential Cancer Chemopreventive Agents, EP Journal of Cancer 41; 1941-1954: (2005).
Germany, "The Absolutely German Drink," contents of beer, 5 pages (2004).
Gilani, "Studies on Antihypertensive and Antispasmodic Activities of Methanol Extract of Acacia nilotica Pods", Phytotherapy Research 13: 665-669 (1999).
Goldstein, et al. Am. J. Gastroenterol. 96:1019-1027 (2001).
Hamberg, et al. J. Bio. Chem. 246:6713-6721 (1971).
Huang, et al. Cancer Res. 51:813-819 (1991).
International Search Report for PCT /US06/30920, Aug. 3, 2007, 3 pages.
International Search Report for PCT/US02/19617, (2003).
International Search Report for PCT/US04/16043, (2005).
International Search Report for PCT/US06/47196, (2007).
Kanematsu, et al. J. Bone Miner Res 12(11):1789-1796 (1997).
Lopes, Curr. Med Res Opin. 8:145-149 (1982).
Meling, et al. Scand. J. Gastroenterol. 31:339-344 (1996).
Newmark, et al., "Beyond Aspirin nature's answer to arthritis, cancer & Alzheimer's disease," hohm press (2000) release 7; pp. 147-151, 248.
Noreen, et al. J. Nat. Prod 61:2-7 (1998).
Pairet, et al. Inflamm. Res 47, Supplement 2s93-s101 (1998).

(56) References Cited

OTHER PUBLICATIONS

Pippa, et al. Scand. J. Gastroenterol. Suppl. 167:32-35 (1989).
Plewig, et al. J. Invest. Dermatol. 65(6):532-536 (1975).
Poullis, et al. J. Gastroenterol. Hepatol. 18:756-762 (2003).
Rahman, M.M., et al., "Conjugated linoleic acid inhibits osteoclast differentiation of RAW264.7 cells by modulating RANKL signaling" J. Lipid Res., 47(8): 1739-1748, (2006).
Ringbom, et al. J. Nat Prod 61:1212-1215 (1998).
Rosemary-Eco Botany, Chemistry, Provital Group, (2006).
Røseth, digest. Liver Dis. 35:607-609 (2003).
Schjerven, et al. Br. J. Dermatol. 149:484-491 (2003).
Shah, et al. Gut 48:339-346 (2001).
Shimamura, et al. Biochem. Biophys. Res. Comm. 289:220-224 (2001).
Shureiqi, et al. Cancer res. 61:6307-6312 (2001).
Sivri, fundam. Clinic. Pharmacol. 18:23-31 (2004).
Smith, et al., "Natural Foam Stabilizing and Bittering Compounds Derived from Hops", American Society of Brewing Chemists, (Jan. 20, 1998).
Subbaramaiah, et al. Cancer Res. 60:2399-2404 (2000).
Suh, et al. Cancer Res. 58:717-723 (1988).
Tagashira, et al., Biosci. Biotech. Biochem. 59(4):740-742 (1996).
The National, Pancreatic Cancer Still a Mystery, 3 pages (Last Updated Jan. 11, 2009).
Thomas m. Newmark and Paul schulick, "Beyond Aspirin nature's answer to arthritis, cancer & alzheimer's disease," hohm press (2000) release 7:pp. 147-151, 248.
Tibble, et al. Drugs Today 37:85-96 (2001).
Tibble, et al. Gut 45:362-366 (1999).
Tobe, et al. Biosci. Biotech. Biochem 61(1):158-159 (1997).
US News and World Report, Palliative Care, 10 pages (posted on Jun. 3, 2008).
Vanhoenacker, et al, "Analysis of iso-a-acids and reduced iso-a-acids in beer . . . ", Journal of Chromatography, Science, 1035: 53-61 (2004).
Wang, et al. Free Radical Biology & Medicine 27:612-616 (1999).
Ward, et al., Therapeutic Potential of Phosphoinositide 3-Kinase Inhibitors, Chemistry & Biology, vol. 10, 207-210, Mar. 2003.
Warner, et al. Proc Natl Acad Sci USA 96:7563-7568 (1999).
Yamamoto, et al. Abstract—Prostaglandins & Other Lipid Mediators 59:1-235 (1999).
Yamamoto, FEBS Letters 465:103-106 (2000).
Yui, et al. Biol. Pharm. Bull. 26:753-760 (2003).
Extended European Search Report issued in European Patent Application No. 08732208.7 dated May 24, 2012.
Tripp, M. et al. "Hop and Modified Hop Extracts have Potent in Vitro Anti-Inflammatory Properties." ACTA Horticulturae. vol. 668. pp. 217-228. 2005.
Kuo, Chi-Li et al. "The Anti-Inflammatory Potential of Berberine in vitro and in vivo." Cancer Letters. vol. 203/ No. 2. pp. 127-137. Jan. 2004.
Fiebich, B.L. et al. "Effects of caffeine and paracetamol alone or in combination with acetylsalicylic acid on prostaglandin E2 synthesis in rat microglial cells." Neuro Pharmacology. vol. 39 / No. 11. pp. 2205-2213. Aug. 23, 2000.
United States Office Action issued in U.S. Appl. No. 12/626,392 dated Jul. 8, 2011.
European Search Report issued in European Application No. 13000201.7 dated Oct. 23, 2013.
Iannonne F, Lapadula G. "The pathophysiology of osteoarthritis." Aging Clin Exp Res., 2003, vol. 15, 364-72.
European Search Report issued in Application No. 13000201.7 dated Jul. 2, 2013.
Puel C et al: "Preventive effect of Abelmoschus manihot (L.) Medik. on bone loss in the ovariectomised rats", Journal of Ethnopharmacology, vol. 99, No. 1, May 2005, pp. 55-60, XP027757260, ISSN: 0378-8741.
Abstract of Liu I M et al: "Myricetin as the active principle of Abelmoschus moschatus to lower plasma glucose in streptozotocin-induced diabetic rats", Medicinal & Aromatic Plants Abstrcts, Scientific Publishers, New Delhi—India, vol. 27, No. 6, Dec. 1, 2005, XP018011725, ISSN: 0250-4367.
Ko Ching-Huai et al: "Myricetin inhibits matrix metalloproteinase 2 protein expression and enzyme activity in colorectal carcinoma cells", Molecular Cancer Therapeutics, vol. 4, No. 2, Feb. 2005, pp. 281-290, XP002699079, ISSN: 1535-7163.
Hsu et al: "Myricetin induces human osteoblast differentiation through bone morphogentic protein-2/p38 mitogen-activated protein kinase pathway", Biochemical Pharmacology, Pergamon, Oxford, GB, vol. 73, No. 4, Jan. 7, 2007, pp. 504-514. XP005824608, ISSN: 0006-2952, DOI: 10.1016/J.BCP.2006.10.020.
Li R W et al: "A Cross-Cultural Study: Anti-Inflammatory Activity of Australian and Chinese Plants", Journal of Ethnopharmacology, Elsevier Scientific Publishers LTD, IE, vol. 85, No. 1, Jan. 1, 2003, pp. 25-32, XP001188263, ISSN: 0378-8741, DOI:10.1016/S0378-8741(02)00336-7.

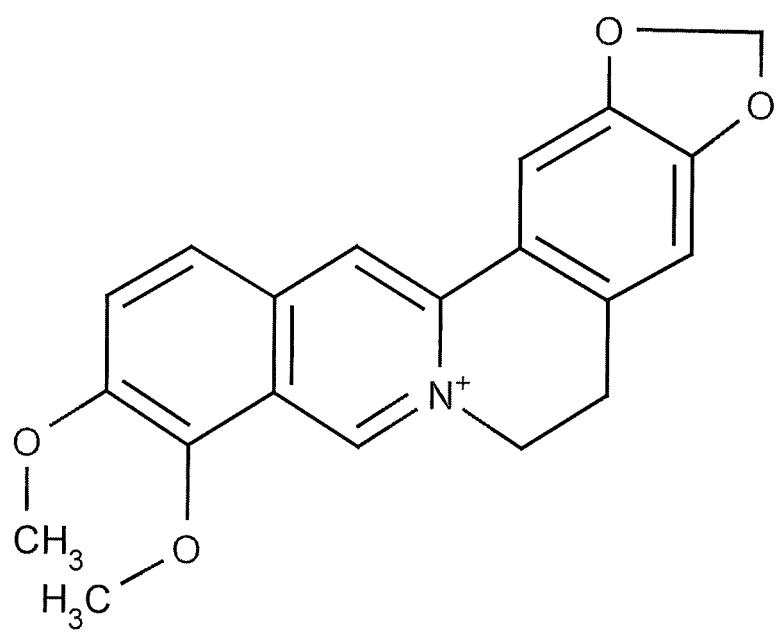

METHODS AND COMPOSITIONS FOR PROMOTING BONE AND JOINT HEALTH

CROSS-REFERENCE TO RELATED APPLICATIONS

This patent application claims priority to U.S. provisional application Ser. No. 60/918,727 filed on Mar. 19, 2007.

BACKGROUND OF THE INVENTION

1. Field of the Invention

The present invention relates generally to methods and compositions that can be used to promote bone and joint health through amelioration, stabilization or repair of damage associated with various pathophysiological conditions.

2. Description of the Related Art

Millions daily suffer damage to joint and bone tissues, either from the normal bumps and bruises of every day life or as a result of various disease conditions. Osteoarthritis, rheumatoid arthritis, and osteoporosis represent the most prevalent diseases influencing bone and joint health. Furthermore, other diseases not generally associated with bone or joint health, such as systemic lupus erythematosus, for example, may have elements affecting bones or joints structure and function.

Osteoarthritis (OA) is an age-related joint disorder that affects more than 40 million Americans (Hinton et al, "Osteoarthritis: Diagnosis and therapeutic considerations." *Am Fam Physician.* 65:841-8, 2002; Lawrence et al, "Estimates of the prevalence of arthritis and selected musculoskeletal disorders in the United States." *Arthritis Rheum.* 41:778-99; 2004). The disease affects the entire joint structure, and is characterized pathologically by focal areas of articular cartilage loss in synovial joints, varying degrees of osteophyte formation (bony outgrowths at the cartilage margins), subchondral bone change, and synovitis. Although OA was historically regarded solely as a degenerative form of arthritis, there is increasing evidence for inflammation as a vital component of OA. Signs of synovial inflammation are present in the many symptoms of OA: joint swelling and effusion, stiffness and occasional redness, especially at proximal and distal interpharyngeal joints. Further, elevated levels of inflammatory cytokines (interleukin-1 beta [IL-1β] and tumor necrosis factor alpha [TNFα]) have been observed in OA synovial fluid. These cytokines, which are primarily synthesized by chondrocytes, appear to play a major part in the destruction of cartilage tissue through the induction of matrix metalloproteinases (MMPs), nitric oxide (NO) and prostaglandin $E_2$ ($PGE_2$). (see, for example, Dieppe & Lohmander, "Pathogenesis and management of pain in osteoarthritis." *Lancet.* 365:965-73; 2005; Felson et al, "Osteoarthritis: New insights". *Ann Intern Med.* 133:635-46; 2000; Goldring, "The role of the chondrocyte in osteoarthritis." *Arthritis Rheum* 43:1916-26; 2000; van der Kraan & van der Berg, "Anabolic and destructive mediators in osteoarthritis." *Curr Opin Nutr Metab Care.* 3:205-11; 2000; Pelletier et al, "Osteoarthritis, an inflammatory disease: Potential implication for the selection of new therapeutic targets." *Arthritis Rheum.* 44:1237-47; 2001; Iannorme F, Lapadula G. "The pathophysiology of osteoarthritis." *Aging Clin Exp Res.* 15:364-72; 2003).

Rheumatoid arthritis (RA) is a systemic inflammatory disorder that affects 1% of the American population, and approximately three times as many women as men are affected by this disorder. RA, which can be a self-limiting condition or a debilitating chronic disease leading to joint destruction and deformity, is characterized by joint inflammation, and the predominant symptoms include pain, stiffness and swelling of peripheral joints. (see, for example, Lee D M, Weinblatt M E. "Rheumatoid arthritis". *Lancet.* 358: 903-11; 2001; Rindfleisch J A, Muller D. "Diagnosis and management of rheumatoid arthritis." *Am Fam Physician.* 72:1049-50; 2005; and Doan T, and Massarotti E. "Rheumatoid arthritis: An overview of new and emerging therapies." *J Clin Pharmacol.* 45:751-62; 2005).

The sequence of events in RA is thought to be initiated by CD4+ T cells, which upon recognizing arthritogenic antigens in synovial tissue, activate macrophages, monocytes and synovial fibroblasts. The activated macrophages, monocytes and synovial fibroblasts then secrete numerous inflammatory cytokines like interleukin-1 (IL-1), IL-6 and tumor necrosis factor α; in addition, these activated cells also secrete matrix metalloproteinases, which are responsible for the proteolytic breakdown of bone and cartilage tissue. Other mediators of inflammation induced by the pro-inflammatory cytokines, and which contribute to the pathology in affected joints include prostaglandin $E_2$ ($PGE_2$) and nitric oxide. (see, for example, Lee D M, Weinblatt M E., Rheumatoid arthritis. "*Lancet.* 358:903-11; 2001; Bingham 3rd CO. "The pathogenesis of rheumatoid arthritis: Pivotal cytokines involved in bone degradation and inflammation." *J Rheumatol.* 29 (suppl 65):3-9; 2002; and Doan T, and Massarotti E. "Rheumatoid arthritis: An overview of new and emerging therapies." *J Clin Pharmacol.* 45:751-62; 2005).

Osteoporosis is a disease characterized by low bone mass and deterioration of bone structure resulting in bone fragility and increased risk of fracture. The World Health Organization has defined osteoporosis as a bone mineral density (BMD) value more than 2.5 standard deviations below the mean for normal young White women. Individuals with osteoporosis are at high risk of suffering one or more fractures, injuries that can often be physically debilitating and potentially lead to a downward spiral in physical and mental health. There are a variety of different types of osteoporosis. "Primary osteoporosis" is the most common form of the disease and is characterized as osteoporosis that is not caused by some other specific disorder. If the bone loss has been caused by specific diseases or medications then it is referred to as "secondary osteoporosis."

According to the Surgeon General of the United States "the 1.5 million osteoporotic fractures in the United States each year lead to more than half a million hospitalizations, over 800,000 emergency room encounters, more than 2,600,000 physician office visits, and the placement of nearly 180,000 individuals into nursing homes. Hip fractures are by far the most devastating type of fracture, accounting for about 300,000 hospitalizations each year. Caring for these fractures is expensive. Studies show that annual direct care expenditures for osteoporotic fractures range from $12 to $18 billion per year in 2002 dollars. Indirect costs (e.g., lost productivity for patients and caregivers) likely add billions of dollars to this figure. These costs could double or triple in the coming decades." See "Bone Health and Osteoporosis: A Report of the Surgeon General (2004)" published at http://www.surgeongeneral.gov/library/bonehealth/content.html (last viewed on Feb. 26, 2008).

Newer methods and compositions for promoting bone and joint health are required since many of the conditions of impaired bone or joint health are or become chronic in nature, thereby necessitating long term therapies. One area for exploration would include botanical based products having proven long term histories of safe use. Two potential candidates are berberine and substituted 1,3-cyclopentadione compounds which may either be isolated from hops or derived from hops.

Berberine (7,8,13,13a-tetrahydro-9,10-dimethoxy-2,3-(methylenedioxy)-berbinium), an alkaloid most commonly associated with extracts from plants of the *Berberis* species, has a history of safety and has known widespread use in traditional medicine for the treatment of a number of conditions ranging from diabetes (See, for example, Leng, S H., et al., "Therapeutic effects of berberine in impaired glucose tolerance rats and its influence on insulin secretion." Acta Pharmacol Sin. 25 (4):496-502; 2004), or for protozoal, bacterial, or fungal infections (see, for example, Sabir, M., et al., "Experimental study of the antitrachoma action of berberine", Indian J Med. Res. 64 (8): 1160-7, 1976; Mohan, M., et al., "Berberine in trachoma. (A clinical trial)." Indian J Opthalmol. 30 (2):69-75, 1982); Mekawi, M., "Effect of berberine alkaloid on cholera Vibro and its endotoxin." J Egypt Med. Assoc. 49 (8):554-9, 1966; or Albal, M V., et al., "Clinical evaluation of berberine in mycotic infections." Indian J Opthalmol. 34:91-2; 1986). Berberine has also been used septic shock and graft versus host disease (Upadhyay, S., et al., U.S. Pat. No. 6,291,483) and investigated for its anti-inflammatory properties as a potential arthritis treatment modality (Ivanovska, N., and Philipov, S., "Study on the anti-inflammatory action of *Berberis vulgaris* root extract, alkaloid fractions and pure alkaloids.", Int. J. Immunopharmac., 18 (10: 553-561, 1996).

The inventors have previously reported on a number of compounds either isolated from hops or derived from hops (alpha acids, beta acids, prenylflavonoids, chalcones, isoalpha acids, and reduced isoalpha acids) which display activity against numerous conditions including inflammation, minor pain, and arthritic conditions (see, for example, U.S. 2003/0008021; US 2003/0113393; US 2004/0115290; or US 2004/0151792). The inventors have found and report herein among other things the unexpected results that berberine may act synergistically with substituted 1,3-cyclopentadione compounds which may either be isolated from hops or derived from hops to promote bone and joint health. The inventors additionally report on combinations of botanically derived compounds which may be used to promote joint and bone health.

SUMMARY OF THE INVENTION

The present invention relates generally to methods and compositions for promoting bone and joint health in mammals. In some instances the subject may have a disease or condition such as osteroarthritis, rheumatoid arthritis, an autoimmune disorder, or osteoporosis. The promotion of bone and joint health may be effectuated through a reduction or cessation of the conditions or factors producing deleterious effects in the affected tissue. Alternatively, the present invention may be used modulate repair mechanism processes to either retard or stabilize tissue damage or to promote repair in the affected tissues. The methods and compositions described employ combinations of berberine and substituted 1,3-cyclopentadione compounds (which may either be isolated from hops or derived from hops), or alternatively, combinations of botanically derived compounds which may be used to promote joint and bone health.

A first embodiment of the invention provides methods to promote bone and joint health in a mammal in need. Here the method comprises comprising administering to the mammal a composition comprising a therapeutically effective amount of berberine or a pharmaceutically acceptable salt thereof as a first component and as a second component a therapeutically effective amount of a substituted 1,3-cyclopentadione compound selected from the group consisting of rho dihydroisoalpha acids and tetrahydroisoalpha acids or pharmaceutically acceptable salts thereof.

A second embodiment provides compositions to promote bone and joint health in a mammal where the compositions comprise a therapeutically effective amount of berberine or a pharmaceutically acceptable salt thereof as a first component and as a second component a therapeutically effective amount of a substituted 1,3-cyclopentadione compound selected from the group consisting of rho dihydroisoalpha acids and tetrahydroisoalpha acids or pharmaceutically acceptable salts thereof.

Methods to promote bone and joint health in a mammal in need are described in another embodiment. Here the compositions of the method comprise from about 10 mg to about 800 mg of berberine or a pharmaceutically acceptable salt thereof and from about 10 mg to about 800 mg of a tetrahydroisoalpha acid or a pharmaceutically acceptable salt thereof, wherein the tetrahydroisoalpha acid is selected from the group consisting of 4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; and (4R,5S)-3,4-dihydroxy-2-(3-methylbutanoyl)-5-(3-methylbutyl)-4-(4-methylpentanoyl)cyclopent-2-en-1-one.

Composition for promoting bone and joint health in a mammal in need comprising from about 10 mg to about 800 mg of berberine or a pharmaceutically acceptable salt thereof and from about 10 mg to about 800 mg of a tetrahydroisoalpha acid or a pharmaceutically acceptable salt thereof, wherein the tetrahydroisoalpha acid is selected from the group consisting of 4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4- ethylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; and (4R,5S)-3,4-dihydroxy-2-(3-methylbutanoyl)-5-(3-methylbutyl)-4-(4-methylpentanoyl)cyclopent-2-en-1-one are described in yet another embodiment.

In still further embodiments of the invention, methods to promote bone and joint health in a mammal in need are described where the compositions of the methods comprise from about 9 mg to about 720 mg of berberine or a pharmaceutically acceptable salt thereof and from about 20 mg to about 1600 mg of a rho dihydroisoalpha acid or a pharmaceutically acceptable salt thereof, wherein the rho dihydroisoalpha acid is selected from the group consisting of (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1S)-hydroxy-4-methylpent-3-en 1-yl]-2-(2-methylpropanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one.

Additionally, compositions to promote bone and joint health in a mammal in need wherein the composition comprises from about 9 mg to about 720 mg of berberine or a pharmaceutically acceptable salt thereof and from about 20 mg to about 1600 mg of a rho dihydroisoalpha acid or a pharmaceutically acceptable salt thereof are described, wherein the rho dihydroisoalpha acid is selected from the group consisting of (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1S)-hydroxy-4- methylpent-3-en-1-yl]-2-(3-methylbutanoyl)-5-(3-methyl-but-2-en-1-yl)cyclopent-2-en-1-one; (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one.

Another embodiment further describes methods to promote bone and joint health in a mammal in need. The methods of this embodiment comprise administering to the mammal a composition comprising therapeutically effective amounts of at least two members selected from the group consisting of *Abelmoschus, Acacia* extract, African Devil's claw, Arthred bovine, Arthred porcine, *Astragalus*, Berberine, Black cohosh, Bonepep, Bonestein, Chicken Collagen, Curcumin, Devil's Claw, DHEA, *Dioscorea*, Flaxseed, FOS, Fructus Ligustri, Genistein, Glabridin, Glucosamine, Green tea, Green Tea Polyphenols, Hesperidin, Hyaluronic Acid, Inulin, Ipriflavone, Linoleic Acid, MBP, MCHA, Oleanolic Acid, Oleuropein, Olive oil, Osteosine, Parthinolide, *Perilla* oil, Phloridzin, Puerariae radix, *Punica granatum*, Quercetin, Red yeast rice, Resveratrol, RIAA, Rosemary, Rutin, THIAA, Vitamin K2, and *Withania*.

A further embodiment provides compositions to promote bone and joint health in a mammal in need. These compositions comprise therapeutically effective amounts of at least two members selected from the group consisting of *Abelmoschus, Acacia* extract, African Devil's claw, Arthred bovine, Arthred porcine, *Astragalus*, Berberine, Black cohosh, Bonepep, Bonestein, Chicken Collagen, Curcumin, Devil's Claw, DHEA, *Dioscorea*, Flaxseed, FOS, Fructus Ligustri, Genistein, Glabridin, Glucosamine, Green tea, Green Tea Polyphenols, Hesperidin, Hyaluronic Acid, Inulin, Ipriflavone, Linoleic Acid, MBP, MCHA, Oleanolic Acid, Oleuropein, Olive oil, Osteosine, Parthinolide, *Perilla* oil, Phloridzin, Puerariae radix, *Punica granatum*, Quercetin, Red yeast rice, Resveratrol, RIAA, Rosemary, Rutin, THIAA, Vitamin K2, and *Withania*.

BRIEF DESCRIPTION OF THE FIGURES

FIG. 1 graphically displays the chemical structure of 7,8,13,13a-tetrahydro-9,10-dimethoxy-2,3-(methylenedioxy)-berbinium; also known as berberine.

DETAILED DESCRIPTION OF THE INVENTION

The present invention relates generally to methods and compositions for promoting bone and joint health in mammals in need. In some instances the subject may have a disease or condition such as osteoarthritis, rheumatoid arthritis, an autoimmune disorder, or osteoporosis. The promotion of bone and joint health may be effectuated through a reduction or cessation of the conditions or factors producing deleterious effects in the affected tissue. Alternatively, the present invention may be used modulate repair mechanism processes to either retard or stabilize tissue damage or to promote repair in the affected tissues. The methods and compositions described employ combinations of berberine and substituted 1,3-cyclopentadione compounds (which may either be isolated from hops or derived from hops), or alternatively, combinations of botanically derived compounds which may be used to promote joint and bone health.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of DNA technology include Sambrook et al., Molecular Cloning: A Laboratory Manual, 2nd Ed., Cold Spring Harbor Laboratory Press, New York (1989); and Kaufman et al., Eds., Handbook of Molecular and Cellular Methods in Biology in Medicine, CRC Press, Boca Raton (1995). Standard reference works setting forth the general principles of pharmacology include Goodman and Gilman's The Pharmacological Basis of Therapeutics, 11th Ed., McGraw Hill Companies Inc., New York (2006).

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. Additionally, as used herein, unless specifically indicated otherwise, the word "or" is used in the "inclusive" sense of "and/or" and not the "exclusive" sense of "either/or." The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The methods and compositions of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses.

A first embodiment of the invention describes methods to promote bone and joint health in a mammal in need. In this embodiment the methods comprise administering to the mammal a composition comprising a therapeutically effective amount of berberine or a pharmaceutically acceptable salt thereof as a first component and as a second component a therapeutically effective amount of a substituted 1,3-cyclopentadione compound selected from the group consisting of rho dihydroisoalpha acids and tetrahydroisoalpha acids or pharmaceutically acceptable salts thereof.

In some aspects of this embodiment, the composition of the method comprises a first component and a second component in a synergistic ratio.

In other aspects, the rho dihydroisoalpha acid is selected from the group consisting of (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one; (4S,5R)-3,4-dihydroxy-4-[(1S)-hydroxy-4-methylpent-3-en-1-yl]2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one.

In still other aspects of this embodiment, the tetrahydroisoalpha acid is selected from the group consisting of 4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; and (4R,5S)-3,4-dihydroxy-2-(3-methylbutanoyl)-5-(3-methylbutyl)-4-(4-methylpentanoyl)cyclopent-2-en-1-one.

In some aspects the second component is derived from hops, while in other aspects the compositions further comprise a pharmaceutically acceptable excipient selected from the group consisting of coatings, isotonic and absorption delaying agents, binders, adhesives, lubricants, disintergrants, coloring agents, flavoring agents, sweetening agents, absorbants, detergents, and emulsifying agents. In yet other aspects the composition further comprises one or more members selected from the group consisting of antioxidants, vitamins, minerals, proteins, fats, and carbohydrates.

In another aspect, the method comprises administering to the mammal a composition which comprises from about 10 mg to about 800 mg of berberine or a pharmaceutically acceptable salt thereof and from about 10 mg to about 800 mg of a tetrahydroisoalpha acid or a pharmaceutically acceptable salt thereof, wherein the tetrahydroisoalpha acid is selected from the group consisting of 4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; and (4R,5S)-3,4-dihydroxy-2-(3-methylbutanoyl)-5-(3-methylbutyl)-4-(4-methylpentanoyl)cyclopent-2-en-1-one.

In yet another aspect, the method comprises administering to the mammal a composition which comprises from about 9 mg to about 720 mg of berberine or a pharmaceutically acceptable salt thereof and from about 20 mg to about 1600 mg of a rho dihydroisoalpha acid or a pharmaceutically acceptable salt thereof, wherein the rho dihydroisoalpha acid is selected from the group consisting of (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one As used herein, the phrase "promote bone health" shall refer to those conditions wherein the methods and compositions of the invention may result in (a) reduced localized pain and inflammation at a site of bone damage; (b) stabilization of bone structure and integrity; (c) modulation of the mechanism(s) to prevent cell based destruction of bone tissue; (d) enhancing repair of damaged bone tissue by increasing bone mineralization; or (e) modulation of the equilibrium between normal bone deposition and reformation. Representative diseases or conditions wherein use of the methods and compositions of the invention include, without limitation, osteoporosis, osteopenia, rickets, osteoarthritis, autoimmune diseases, and rheumatoid arthritis.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or compounds, but may also include additional features or compounds.

As used herein, the terms "derivatives" or a matter "derived" refer to a chemical substance related structurally to another substance and theoretically obtainable from it, i.e. a substance that can be made from another substance. Derivatives can include compounds obtained via a chemical reaction.

As used herein, "berberine" refers to 7,8,13,13a-tetrahydro-9,10-dimethoxy-2,3-(methylenedioxy)-berbinium. Berberine, an alkaloid, is most commonly associated with but not limited to extracts from plants of the *Berberis* species.

As used herein, "substituted 1,3-cyclopentadione compounds" refers to those compounds generally described as reduced isoalpha acids commonly associated with hops and beer production. The substituted 1,3-cyclopentadione compounds refers to the dihydroisoalpha acids (RIAA), tetrahydroisoalpha acids ("THIAA") and hexahydroisalpha acids ("HHIAA"). Examples of reduced isoalpha acids (RIAA) include without limitation dihydroisoalpha acids, more specifically Rho dihydroisoalpha acids (Table 1), tetrahydroisoalpha acid (Table 2), and hexahydroisoalpha acids (Table 3), and their derivatives. "Rho" refers to those reduced isoalpha acids wherein the reduction is a reduction of the carbonyl group in the 4-methyl-3-pentenoyl side chain.

TABLE 1

| Rho dihydroisoalpha acids | | |
|---|---|---|
| Chemical Name | Synonym | Structure |
| (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one | rho (6S) cis n iso-alpha acid | |
| (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one | rho (6R) cis n iso-alpha acid | |
| (4R,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one | rho (6R) trans n iso-alpha acid | |

TABLE 1-continued

| Rho dihydroisoalpha acids | | |
|---|---|---|
| Chemical Name | Synonym | Structure |
| (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one | rho (6S) trans n iso-alpha acid | |
| (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one | rho (6R) cis rho n iso-alpha acid | |
| (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one | rho (6S) cis n iso-alpha acid | |
| (4S,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one | (6S) trans rho n iso-alpha acid | |

TABLE 1-continued

Rho dihydroisoalpha acids

| Chemical Name | Synonym | Structure |
| --- | --- | --- |
| (4S,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one | rho (6R) trans n iso-alpha acid | 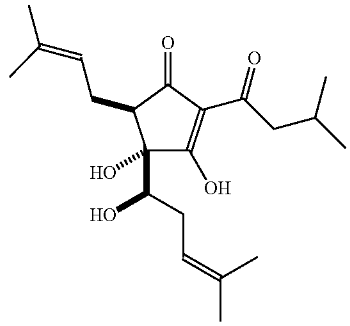 |
| (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | rho (6S) cis co iso-alpha acid | 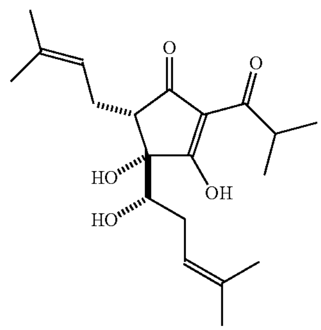 |
| (4S,5S)-3,4-dihydroxy-4-[(1R)-hydroxy-4-methylpent-3-en-1-yl]-5-(3-methylbut-2-en-1-yl)-2-(2-methylpropanoyl)cycopent-2-en-1-one | rho (6R) cis co iso-alpha acid | 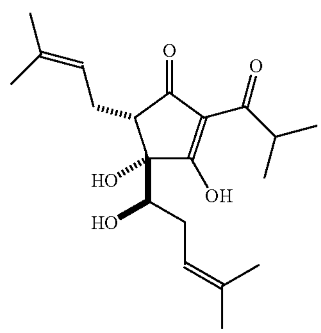 |
| (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | rho (6R) trans co iso-alpha acid | 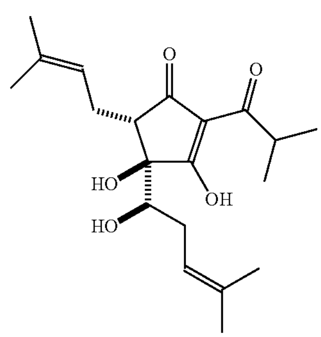 |

TABLE 1-continued

Rho dihydroisoalpha acids

| Chemical Name | Synonym | Structure |
|---|---|---|
| (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | rho (6S) trans co iso-alpha acid | 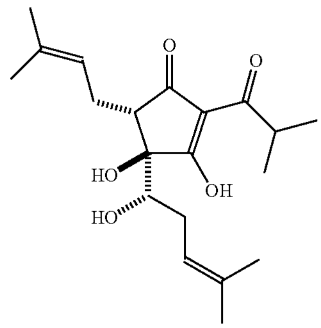 |
| (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | rho (6R) cis co iso-alpha acid | 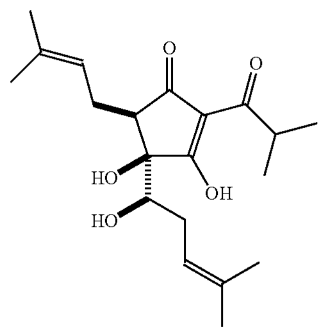 |
| (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | rho (6S) cis co iso-alpha acid | 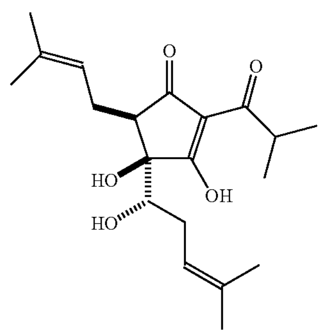 |
| (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one | rho (6S) trans co iso-alpha acid | 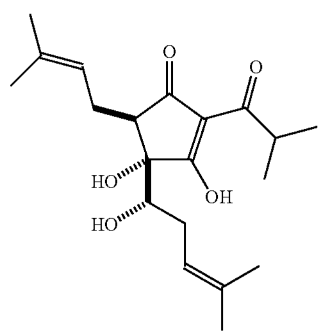 |

TABLE 1-continued

| Rho dihydroisoalpha acids | | |
|---|---|---|
| Chemical Name | Synonym | Structure |
| (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | rho (6R) trans co iso-alpha acid | |
| (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | rho (6S) cis ad iso-alpha acid | |
| (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | rho (6R) cis ad iso-alpha acid | |
| (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | rho (6R) trans ad iso-alpha acid | |

TABLE 1-continued

| Rho dihydroisoalpha acids | | |
|---|---|---|
| Chemical Name | Synonym | Structure |
| (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | rho (6S) trans ad iso-alpha acid | |
| (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | rho (6R) cis ad iso-alpha acid | |
| (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | rho (6S) cis ad iso-alpha acid | |
| (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | rho (6S) trans ad iso-alpha acid | |

TABLE 1-continued

| Rho dihydroisoalpha acids | | |
|---|---|---|
| Chemical Name | Synonym | Structure |
| (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | rho (6R) trans ad iso-alpha acid | |

TABLE 2

| Tetrahydroisoalpha acids | | |
|---|---|---|
| Chemical Name | Synonym | Structure |
| (4R,5S)-3,4-dihydroxy-2-(3-methylbutanoyl)-5-(3-methylbutyl)-4-(4-methylpentanoyl)cyclopent-2-en-1-one | tetrahydro cis n iso-alpha acid | |
| (4S,5S)-3,4-dihydroxy-2-(3-methylbutanoyl)-5-(3-methylbutyl)-4-(4-methylpentanoyl)cyclopent-2-en-1-one | tetrahydro trans n iso-alpha acid | |
| (4S,5R)-3,4-dihydroxy-2-(3-methylbutanoyl)-5-(3-methylbutyl)-4-(4-methylpentanoyl)cyclopent-2-en-1-one | tetrahydro cis n iso-alpha acid | |

TABLE 2-continued

| Tetrahydroisoalpha acids | | |
|---|---|---|
| Chemical Name | Synonym | Structure |
| (4R,5R)-3,4-dihydroxy-2-(3-methylbutanoyl)-5-(3-methylbutyl)-4-(4-methylpentanoyl)cyclopent-2-en-1-one | tetrahydro trans n iso-alpha acid | |
| (4R,5S)-3,4-dihydroxy-5-(3-methylbutyl)-4-(4-methylpentanoyl)-2-(3-methylpropanoyl)cyclopent-2-en-1-one | tetrahydro cis co iso-alpha acid | |
| (4S,5S)-3,4-dihydroxy-5-(3-methylbutyl)-4-(4-methylpentanoyl)-2-(3-methylpropanoyl)cyclopent-2-en-1-one | tetrahydro trans co iso-alpha acid | |
| (4S,5R)-3,4-dihydroxy-5-(3-methylbutyl)-4-(4-methylpentanoyl)-2-(3-methylpropanoyl)cyclopent-2-en-1-one | tetrahydro cis co iso-alpha acid | |

TABLE 2-continued

Tetrahydroisoalpha acids

| Chemical Name | Synonym | Structure |
| --- | --- | --- |
| (4R,5R)-3,4-dihydroxy-5-(3-methylbutyl)-4-(4-methylpentanoyl)-2-(3-methylpropanoyl)cyclopent-2-en-1-one | tetrahydro trans co iso-alpha acid | 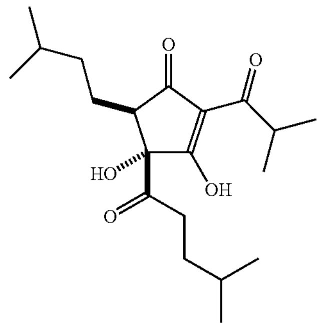 [SMILES: CC(C)CCC(=O)[C@]1(O)C(O)=C(C(=O)C(C)C)C(=O)[C@@H]1CCC(C)C] |
| (4R,5S)-3,4-dihydroxy-2-(2-methylbutanoyl)-5-(3-methylbutyl)-4-(4-methylpentanoyl)cyclopent-2-en-1-one | tetrahydro cis ad iso-alpha acid | 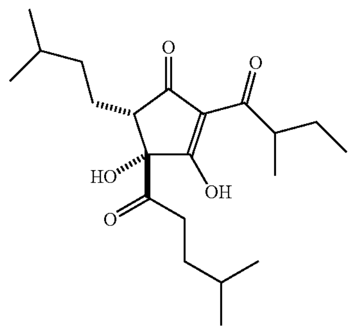 [SMILES: CCC(C)C(=O)C1=C(O)[C@@](O)(C(=O)CCC(C)C)[C@H](CCC(C)C)C1=O] |
| (4S,5S)-3,4-dihydroxy-2-(2-methylbutanoyl)-5-(3-methylbutyl)-4-(4-methylpentanoyl)cyclopent-2-en-1-one | tetrahydro trans ad iso-alpha acid | 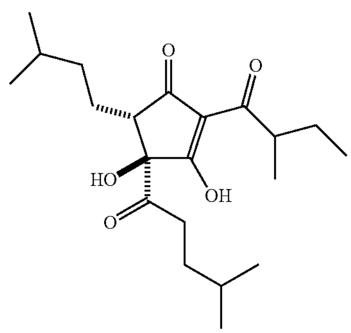 [SMILES: CCC(C)C(=O)C1=C(O)[C@](O)(C(=O)CCC(C)C)[C@H](CCC(C)C)C1=O] |
| (4S,5R)-3,4-dihydroxy-2-(2-methylbutanoyl)-5-(3-methylbutyl)-4-(4-methylpentanoyl)cyclopent-2-en-1-one | tetrahydro cis ad iso-alpha acid | 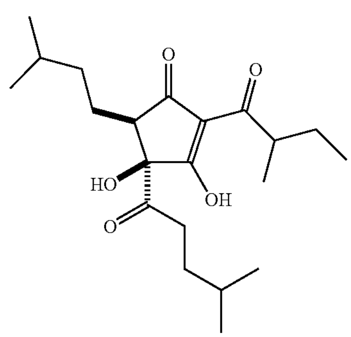 [SMILES: CCC(C)C(=O)C1=C(O)[C@](O)(C(=O)CCC(C)C)[C@@H](CCC(C)C)C1=O] |

TABLE 2-continued

| | Tetrahydroisoalpha acids | |
|---|---|---|
| Chemical Name | Synonym | Structure |
| (4R,5R)-3,4-dihydroxy-2-(2-methylbutanoyl)-5-(3-methylbutyl)-4-(4-methylpentanoyl)cyclopent-2-en-1-one | tetrahydro trans ad iso-alpha acid | |

TABLE 3

| | Hexahydroisoalpha acids | |
|---|---|---|
| Chemical Name | Synonym | Structure |
| (4S,5S)-3,4-dihydroxy-4-[(1S)-1-hydroxy-4-methylpentyl]-2-(3-methylbutanoyl)-5-(3-methylbutyl)cyclopent-2-en-1-one | hexahydro (6S) cis n iso-alpha acid | |
| (4S,5S)-3,4-dihydroxy-4-[(1R)-1-hydroxy-4-methylpentyl]-2-(3-methylbutanoyl)-5-(3-methylbutyl)cyclopent-2-en-1-one | hexahydro (6R) cis n iso-alpha acid | |
| (4R,5S)-3,4-dihydroxy-4-[(1R)-1-hydroxy-4-methylpentyl]-2-(3-methylbutanoyl)-5-(3-methylbutyl)cyclopent-2-en-1-one | hexahydro (6R) trans n iso-alpha acid | |

TABLE 3-continued

| Hexahydroisoalpha acids | | |
|---|---|---|
| Chemical Name | Synonym | Structure |
| (4R,5S)-3,4-dihydroxy-4-[(1S)-1-hydroxy-4-methylpentyl]-2-(3-methylbutanoyl)-5-(3-methylbutyl)cyclopent-2-en-1-one | hexahydro (6S) trans n iso-alpha acid | |
| (4R,5R)-3,4-dihydroxy-4-[(1R)-1-hydroxy-4-methylpentyl]-2-(3-methylbutanoyl)-5-(3-methylbutyl)cyclopent-2-en-1-one | hexahydro (6S) cis n iso-alpha acid | |
| (4R,5R)-3,4-dihydroxy-4-[(1S)-1-hydroxy-4-methylpentyl]-2-(3-methylbutanoyl)-5-(3-methylbutyl)cyclopent-2-en-1-one | hexahydro (6S) cis n iso-alpha acid | |
| (4S,5R)-3,4-dihydroxy-4-[(1S)-1-hydroxy-4-methylpentyl]-2-(3-methylbutanoyl)-5-(3-methylbutyl)cyclopent-2-en-1-one | hexahydro (6S) trans n iso-alpha acid | |

TABLE 3-continued

| Hexahydroisoalpha acids | | |
|---|---|---|
| Chemical Name | Synonym | Structure |
| (4S,5R)-3,4-dihydroxy-4-[(1R)-1-hydroxy-4-methylpentyl]-2-(3-methylbutanoyl)-5-(3-methylbutyl)cyclopent-2-en-1-one | hexahydro (6R) trans n iso-alpha acid | |
| (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | hexahydro (6S) cis co iso-alpha acid | |
| (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | hexahydro (6R) cis co iso-alpha acid | |
| (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | hexahydro (6R) trans co iso-alpha acid | |

TABLE 3-continued

Hexahydroisoalpha acids

| Chemical Name | Synonym | Structure |
|---|---|---|
| (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | hexahydro (6S) trans co iso-alpha acid | 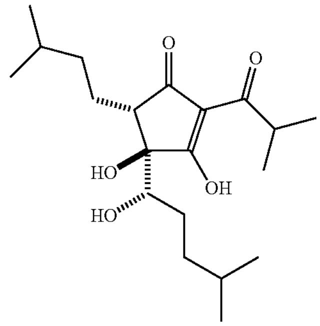 [SMILES: CC(C)CC[C@@H]1C(=O)C(C(=O)C(C)C)=C(O)[C@]1(O)[C@@H](O)CCC(C)C] |
| (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | hexahydro (6R) cis co iso-alpha acid | 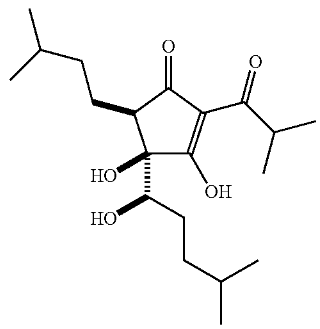 [SMILES: CC(C)CC[C@@H](O)[C@@]1(O)C(O)=C(C(=O)C(C)C)C(=O)[C@@H]1CCC(C)C] |
| (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one | hexahydro (6S) cis co iso-alpha acid | 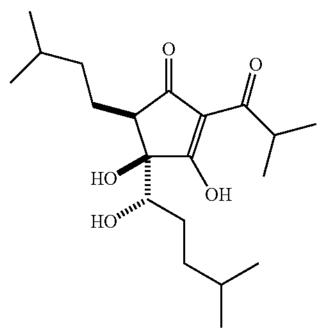 [SMILES: CC(C)CC[C@H](O)[C@@]1(O)C(O)=C(C(=O)C(C)C)C(=O)[C@@H]1CCC(C)C] |
| (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one | hexahydro (6S) trans co iso-alpha acid | 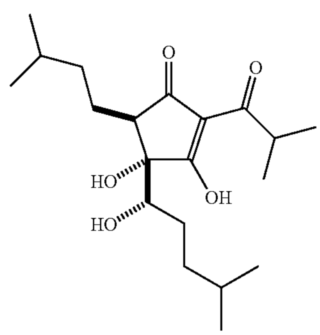 [SMILES: CC(C)CC[C@H](O)[C@]1(O)C(O)=C(C(=O)C(C)C)C(=O)[C@@H]1CCC(C)C] |

TABLE 3-continued

| Hexahydroisoalpha acids | | |
|---|---|---|
| Chemical Name | Synonym | Structure |
| (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one | hexahydro (6R) trans co iso-alpha acid | |
| (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | hexahydro (6S) cis ad iso-alpha acid | |
| (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | hexahydro (6R) cis ad iso-alpha acid | |
| (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | hexahydro (6R) trans ad iso-alpha acid | |

TABLE 3-continued

| Hexahydroisoalpha acids | | |
|---|---|---|
| Chemical Name | Synonym | Structure |
| (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | hexahydro (6S) trans ad iso-alpha acid | |
| (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | hexahydro (6R) cis ad iso-alpha acid | |
| (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | hexahydro (6S) cis ad iso-alpha acid | |
| (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one | hexahydro (6S) trans ad iso-alpha acid | |

TABLE 3-continued

Hexahydroisoalpha acids

| Chemical Name | Synonym | Structure |
| --- | --- | --- |
| (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one | hexahydro (6R) trans ad iso-alpha acid | 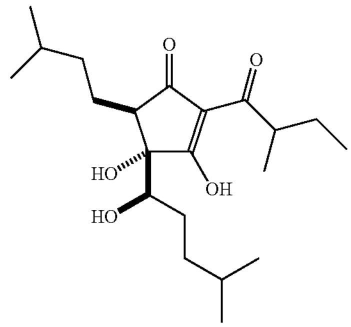 |

In some instances the compounds of the second component are derived from hops. See Verzele, M. and De Keukeleire, D., *Developments in Food Science 27: Chemistry and Analysis of Hop and Beer Bitter Acids*, Elsevier Science Pub. Co., 1991, New York, USA, herein incorporated by reference in its entirety, for a detailed discussion of hops chemistry.

The term "pharmaceutically acceptable" is used in the sense of being compatible with the other ingredients of the compositions and not deleterious to the recipient thereof.

As used herein, "compounds" may be identified either by their chemical structure, chemical name, or common name. When the chemical structure and chemical or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2$H, $^3$H, $^{13}$C, $^{14}$C, $^{15}$N, $^{18}$O, $^{17}$O, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

Compounds according to the invention may be present as salts. In particular, pharmaceutically acceptable salts of the compounds are contemplated. A "pharmaceutically acceptable salt" of the invention is a combination of a compound of the invention and either an acid or a base that forms a salt (such as, for example, the magnesium salt, denoted herein as "Mg" or "Mag") with the compound and is tolerated by a subject under therapeutic conditions. In general, a pharmaceutically acceptable salt of a compound of the invention will have a therapeutic index (the ratio of the lowest toxic dose to the lowest therapeutically effective dose) of 1 or greater. The person skilled in the art will recognize that the lowest therapeutically effective dose will vary from subject to subject and from indication to indication, and will thus adjust accordingly.

As used herein "hop" or "hops" refers to plant cones of the genus *Humulus* which contains a bitter aromatic oil which is used in the brewing industry to prevent bacterial action and add the characteristic bitter taste to beer. More preferably, the hops used are derived from *Humulus lupulus*.

The compounds according to the invention are optionally formulated in a pharmaceutically acceptable vehicle with any of the well known pharmaceutically acceptable carriers, including diluents and excipients (see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated.

The compositions of the invention can be administered by standard routes. The compositions of the invention include those suitable for oral, inhalation, rectal, ophthalmic (including intravitreal or intracameral), nasal, topical (including buccal and sublingual), vaginal, or parenteral (including subcutaneous, intramuscular, intravenous, intradermal, and intratracheal). In addition, polymers may be added according to standard methodologies in the art for sustained release of a given compound.

It is contemplated within the scope of the invention that compositions used to treat a disease or condition will use a pharmaceutical grade compound and that the composition will further comprise a pharmaceutically acceptable carrier. It is further contemplated that these compositions of the invention may be prepared in unit dosage forms appropriate to both the route of administration and the disease and patient to be treated. The compositions may conveniently be presented in dosage unit form be prepared by any of the methods well known in the art of pharmacy. All methods include the step of bringing the active ingredient into association with the vehicle which constitutes one or more auxiliary constituents, In general, the compositions are prepared by uniformly and intimately bringing the active ingredient into association with a liquid vehicle or a finely divided solid vehicle or both, and then, if necessary, shaping the product into the desired composition.

The term "dosage unit" is understood to mean a unitary, i.e. a single dose which is capable of being administered to a patient, and which may be readily handled and packed, remaining as a physically and chemically stable unit dose comprising either the active ingredient as such or a mixture of it with solid or liquid pharmaceutical vehicle materials.

Compositions suitable for oral administration may be in the form of discrete units as capsules, sachets, tablets, soft gels or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, gum arabic, dextran, sodium carboxymethylcellulose, gelatin, methylcellulose and polyvinylpyrrolidone. The active ingredient may also be administered in the form of a bolus, electuary or paste.

Transdermal compositions may be in the form of a plaster, microstructured arrays, sometimes called microneedles, iontophoresis (which uses low voltage electrical current to drive charged drugs through the skin), electroporation (which uses short electrical pulses of high voltage to create transient aqueous pores in the skin), sonophoresis (which uses low frequency ultrasonic energy to disrupt the stratum corneum), and thermal energy (which uses heat to make the skin more permeable and to increase the energy of drug molecules), or via polymer patch.

Liposomal compositions or biodegradable polymer systems may also be used to present the active ingredient for ophthalmic administration.

Compositions suitable for topical administration include liquid or semi-liquid preparations such as liniments, lotions, gels, and oil-in-water or water-in-oil emulsions such as creams, ointments or pastes; or solutions or suspensions such as drops.

In addition to the compositions described above, the compositions of the invention may also be formulated as a depot preparation. Such long-acting compositions may be administered by implantation (e.g. subcutaneously, intraabdominally, or intramuscularly) or by intramuscular injection. Thus, for example, the active ingredient may be formulated with suitable polymeric or hydrophobic materials (for example, as an emulsion in a pharmaceutically acceptable oil), or an ion exchange resin.

As used herein, by "treating" is meant reducing, preventing, and/or reversing the symptoms in the individual to which a compound of the invention has been administered, as compared to the symptoms of an individual not being treated according to the invention. A practitioner will appreciate that the compounds, compositions, and methods described herein are to be used in concomitance with continuous clinical evaluations by a skilled practitioner (physician or veterinarian) to determine subsequent therapy. Hence, following treatment the practitioners will evaluate any improvement in the treatment of the pulmonary inflammation according to standard methodologies. Such evaluation will aid and inform in evaluating whether to increase, reduce or continue a particular treatment dose, mode of administration, etc.

It will be understood that the subject to which a compound of the invention is administered need not suffer from a specific traumatic state. Indeed, the compounds of the invention may be administered prophylactically, prior to any development of symptoms. The term "therapeutic," "therapeutically," and permutations of these terms are used to encompass therapeutic, palliative as well as prophylactic uses. Hence, as used herein, by "treating or alleviating the symptoms" is meant reducing, preventing, and/or reversing the symptoms of the individual to which a compound of the invention has been administered, as compared to the symptoms of an individual receiving no such administration.

The term "therapeutically effective amount" is used to denote treatments at dosages effective to achieve the therapeutic result sought. Furthermore, one of skill will appreciate that the therapeutically effective amount of the compound of the invention may be lowered or increased by fine tuning and/or by administering more than one compound of the invention, or by administering a compound of the invention with another compound. See, for example, Meiner, C. L., "Clinical Trials: Design, Conduct, and Analysis," Monographs in Epidemiology and Biostatistics, Vol. 8 Oxford University Press, USA (1986). The invention therefore provides a method to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect.

It will be appreciated by those of skill in the art that the number of administrations of the compounds according to the invention will vary from patient to patient based on the particular medical status of that patient at any given time including other clinical factors such as age, weight and condition of the mammal and the route of administration chosen.

As used herein, "symptom" denotes any sensation or change in bodily function that is experienced by a patient and is associated with a particular disease, i.e., anything that accompanies "X" and is regarded as an indication of "X"'s existence. It is recognized and understood that symptoms will vary from disease to disease or condition to condition.

A second embodiment of the invention describes compositions to promote bone and joint health in a mammal. Here the compositions comprise a therapeutically effective amount of berberine or a pharmaceutically acceptable salt thereof as a first component and as a second component a therapeutically effective amount of a substituted 1,3-cyclopentadione compound selected from the group from the group consisting of rho dihydroisoalpha acids and tetrahydroisoalpha acids or pharmaceutically acceptable salts thereof.

In some aspects of this embodiment the first component and the second component are in a synergistic ratio.

The rho dihydroisoalpha acid is selected from the group consisting of (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en- 1-one; (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylpropanoyl)-5-(3-methylbut-2-er-1-yl)cyclopent-2-en-1-one; (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one is utilized in other aspects of this embodiment.

In another aspect of this embodiment the tetrahydroisoalpha acid is selected from the group consisting of 4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; and (4R,5S)-3,4-dihydroxy-2-(3-methylbutanoyl)-5-(3-methylbutyl)-4-(4-methylpentanoyl)cyclopent-2-en-1-one.

In some aspects the second component of the composition is derived from hops while in other aspects the composition further comprises a pharmaceutically acceptable excipient selected from the group consisting of coatings, isotonic and absorption delaying agents, binders, adhesives, lubricants, disintergrants, coloring agents, flavoring agents, sweetening agents, absorbants, detergents, and emulsifying agents. Additionally, in still other aspects the composition further comprises one or more members selected from the group consisting of antioxidants, vitamins, minerals, proteins, fats, and carbohydrates.

Another aspect describes compositions comprising from about 10 mg to about 800 mg of berberine or a pharmaceutically acceptable salt thereof and from about 10 mg to about 800 mg of a tetrahydroisoalpha acid or a pharmaceutically acceptable salt thereof, wherein the tetrahydroisoalpha acid is selected from the group consisting of 4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)cyclopent-2-en-1-one; (4R,5S)-3,4-dihydroxy-2-(3-methylbutanoyl)-5-(3-methylbutyl)-4-(4-methylpentanoyl)

cyclopent-2-en-1-one; and (4R,5S)-3,4-dihydroxy-2-(3-methylbutanoyl)-5-(3-methylbutyl)-4-(4-methylpentanoyl)cyclopent-2-en-1-one.

In yet another aspect, the composition comprises from about 9 mg to about 720 mg of berberine or a pharmaceutically acceptable salt thereof and from about 20 mg to about 1600 mg of a rho dihydroisoalpha acid or a pharmaceutically acceptable salt thereof, wherein the rho dihydroisoalpha acid is selected from the group consisting of (4S,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5R)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4R,5S)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4R,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[1-(R)-hydroxy-4-methylpent-3-en-1-yl]-2-(2-methylbutanoyl)-5-(3-methylbut-2-en-1-yl)cyclopent-2-en-1-one; (4S,5R)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5R)-3,4-dihydroxy-4-[(1S)-hydroxy-4-methylpent-3-en-1-yl]-2-(3-methylbutanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylpropanoyl)-5-(3-methylbut-2-en-1-yl)cyclopent-2-en-1-one; (4S,5R)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(3-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-2-(2-methylbutanoyl)-5-(3-methylbut-2-en-1-yl)cyclopent-2-en-1-one; (4S,5S)-3,4-dihydroxy-4-[(1R)-hydroxy-4-methylpent-3-en-1-yl]-5-(3-methylbut-2-en-1-yl)-2-(2-methylpropanoyl)cyclopent-2-en-1-one; (4S,5S)-3,4-dihydroxy-4-[(1S)-hydroxy-4-methylpent-3-en-1-yl]-2-(2-methylbutanoyl)-5-(3-methylbut-2-en-1-yl)cyclopent-2-en-1-one; and (4S,5S)-3,4-dihydroxy-4-[(1S)-hydroxy-4-methylpent-3-en-1-yl]-5-(3-methylbut-2-en-1-yl)-2-(2-methylpropanoyl)cyclopent-2-en-1-one.

Another embodiment of the invention describes methods to promote bone and joint health in a mammal in need where the method comprises administering to the mammal a composition comprising therapeutically effective amounts of at least two members selected from the group consisting of *Abelmoschus, Acacia* extract, African Devil's claw, Arthred bovine, Arthred porcine, *Astragalus*, Berberine, Black cohosh, Bonepep, Bonestein, Chicken Collagen, Curcumin, Devil's Claw, DHEA, *Dioscorea*, Flaxseed, FOS, Fructus Ligustri, Genistein, Glabridin, Glucosamine, Green tea, Green Tea Polyphenols, Hesperidin, Hyaluronic Acid, Inulin, Ipriflavone, Linoleic Acid, MBP, MCHA, Oleanolic Acid, Oleuropein, Olive oil, Osteosine, Parthinolide, *Perilla* oil, Phloridzin, Puerariae radix, *Punica granatum*, Quercetin, Red yeast rice, Resveratrol, Rosemary, Rutin, Vitamin K2, and *Withania*.

In some aspects of the embodiment the composition utilized is a medical food.

A further embodiment describes compositions to promote bone and joint health in a mammal in need. In this embodiment the compositions comprise therapeutically effective amounts of at least two members selected from the group consisting of *Abelmoschus, Acacia* extract, African Devil's claw, Arthred bovine, Arthred porcine, *Astragalus*, Berberine, Black cohosh, Bonepep, Bonestein, Chicken Collagen, Curcumin, Devil's Claw, DHEA, *Dioscorea*, Flaxseed, FOS, Fructus Ligustri, Genistein, Glabridin, Glucosamine, Green tea, Green Tea Polyphenols, Hesperidin, Hyaluronic Acid, Inulin, Ipriflavone, Linoleic Acid, MBP, MCHA, Oleanolic Acid, Oleuropein, Olive oil, Osteosine, Parthinolide, *Perilla* oil, Phloridzin, Puerariae radix, *Punica granatum*, Quercetin, Red yeast rice, Resveratrol, Rosemary, Rutin, Vitamin K2, and *Withania*. In some aspects of this embodiment the composition is a medical food.

As used herein, "medical food" refers to those compositions wherein all of the components are generally regarded as safe (GRAS) and the composition meets the statutory and regulatory requirements for a medical food within the jurisdiction of enforcement.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLES

Example 1

Modified Hop Extracts and Herbal Extracts Modulate TNFα Induced MMP-13 Expression in Human Chondrocyte Cell Line, SW1353

The Model—

The SW1353 human chondrocyte cell line was used as described below.

Materials—

All test materials were provided by Metagenics Inc (San Clemente, Calif.). Test compounds were prepared in dimethyl sufoxide (DMSO) and stored at −20° C. Human TNFα was purchased from Sigma Chemicals (St. Louis, Mo.). MMP-13 kits were purchased from Amersham Biosciences (Piscataway, N.J.).

Cell Culture and Treatment—

The human chondrocyte cell line, SW 1353 was purchased from ATCC (Manassas, Va.) and maintained in L-15 medium in the presence of 10% serum according to manufacturer instructions. Cells were grown and subcultured in 96-well plates at a density of $8 \times 10^4$ cells per well and allowed to reach ~80% confluence overnight. Test compounds in medium were added to the cells at a final concentration of 0.1% DMSO. Following one hour of incubation with the test compounds, TNFα (10 ng/ml) or medium alone was added to the cell wells and incubation continued for 24 hours. The supernatant media was subsequently collected for MMP-13 determination.

Determination of MMP-13: A commercial, non-radioactive procedure for quantification of MMP-13 was used according to the manufacturer's instructions using MMP-13 as a standard. A minimum of 3 wells were used for each test condition.

Statistical Analysis—

The amount of MMP-13 release into the medium was determined by comparison of the MMP-13 generated in the presence or absence of TNFα and test compounds. A minimum of three wells were used for each test condition. The basal MMP-without 13 levels without TNFα stimulation was subtracted from TNF stimulation to determine the TNFα induced MMP-13 expression in the medium and the levels normalized to 100%. The percent activity of test compounds was measured in the presence of TNFα and referred as TNFα induced MMP-13 expression.

Results—

Test compounds at 10 μg/ml or 20 μg/ml were modulated TNFα induced MMP-13 expression (Table 4) in human chondrocyte cells, SW 1353.

TABLE 4

Effect of modified hop extracts and herbal extracts on TNFα induced MMP-13 expression

| Test Compounds | ug/mL | TNFa Stimulated MMP-13 average | SD | Test Compounds | ug/mL | TNFa Stimulated MMP-13 average | SD |
| --- | --- | --- | --- | --- | --- | --- | --- |
| TNF Neg | — | 0% | 17% | Black cohosh | 20 | 63% | 20% |
| TNF pos | 0 | 100% | 28% | Salvia | 20 | 118% | 17% |
| RIAA | 10 | 20% | 11% | Red yeast rice | 20 | 85% | 50% |
| RIAA | 20 | 0% | 7% | Glabridin | 20 | 79% | 61% |
| Kaprex | 10 | 37% | 12% | Resveratrol | 20 | −42% | 6% |
| THIAA | 10 | 34% | 34% | Ipriflavone | 20 | −42% | 7% |
| THIAA | 20 | 3% | 24% | Abelmoschus | 20 | 56% | 53% |
| Tetrex | 10 | 26% | 11% | DHA | 20 | 265% | 41% |
| Acacia | 10 | 73% | 7% | Perilla oil | 20 | 100% | 61% |
| Rosemary | 10 | 25% | 14% | Pelicosanol | 20 | 489% | 687% |
| Oleanolic Acid | 10 | 17% | 23% | Camellia Sinensis | 20 | 159% | 13% |
| Curcumin | 10 | −11% | 0% | Green Tea | 20 | 74% | 16% |
| Trimax | 10 | −8% | 4% | Dioscorea | 20 | 48% | 54% |
| Hyaluronic Acid | 20 | 105% | 55% | Quercetin | 20 | −65% | 18% |
| Glucosamine | 20 | 77% | 41% | Hesperidin | 20 | 13% | 29% |
| Green Tea Polyphenols | 20 | 53% | 15% | Berberine | 20 | −39% | 63% |
| Punica granatum | 20 | 84% | 30% | Flaxseed | 20 | −24% | 1% |
| African Devil's claw | 20 | 58% | 9% | Oleuropein | 20 | −31% | 18% |
| Parthenolide | 20 | 28% | 22% | Olive oil | 20 | −23% | 6% |
| Vitamin C | 20 | 370% | 94% | Rutin | 20 | −7% | 49% |
| MBP | 20 | 90% | 38% | FOS | 20 | −12% | 12% |
| Bonepep | 20 | 114% | 65% | Inulin | 20 | 33% | 61% |
| Bonistein | 20 | −30% | 16% | Linoleic Acid | 20 | 23% | 22% |
| Genistein | 20 | 27% | 18% | Astragalus | 20 | −8% | 44% |
| Vitamin K2 | 20 | 56% | 41% | Chicken Collagen | 20 | −6% | 15% |
| DHEA | 20 | −2% | 45% | Arthred Bovine | 20 | 109% | 143% |
| Withania | 20 | −11% | 11% | Arthred Porcine | 20 | −12% | 22% |
| Potassium Citrate | 20 | 95% | 26% | Osteosine | 20 | −4% | 43% |
| Fructus Ligustri | 20 | 56% | 26% | MCHA | 20 | 11% | 31% |
| Phloridzin | 20 | 77% | 40% | Prune PE | 20 | 321% | 130% |
| Puerariae radix | 20 | 70% | 37% | | | | |

*formula components:
Kaprex (RIAA:Rosemary:Oleanolic acid; 225:112.5:1)
Tetrex (THIAA:Rosemary:Oleanolic acid; 225:112.5:1)
Trimax (RIAA:Curcumin:Rosemary; 2:2:1)

Example 2

Modified Hop Extracts and Herbal Extracts Dose Dependently Modulate TNFα Induced MMP-13 Expression in Human Chondrocyte Cell Line, SW1353

The Model—

The SW1353 human chondrocyte cell line model as described in Example 1.

Cell Culture and Treatment—

Standard chemicals used were described in Example 1. Following one hour of incubation with the test compounds (RIAA, curcumin, DHEA withania, resveratrol, ipriflavone, astragalus, purariae radix, bonistein and parthanolide at multiple concentrations (20, 10, 5 and 1 ug/ml)), the human chondrocyte cell line, SW 1353 was stimulated with TNFα (10 ng/ml) for 24 hrs. MMP-13 levels were measured in the medium as described in the Example 1.

Determination of MMP-13 expression—The MMP-13 levels in the medium were measured as described in Example 1.

Calculations—

The percent of MMP-13 levels in the medium was measured as described in Example 1 in the presence and absence of TNFα.

Median Effect Calculations—

Median effect calculations were performed using CalcuSyn (Biosoft, Ferguson, Mo.), This program utilizes the Median Effects Model of Chou and Talalay (Adv Enzym Regul (1984) 22:27-55) and fits the equation:

$$\log C = \beta_0 + \beta_1 \log [f_a/(1-f_a)] = \epsilon$$

where $f_a$ is the factional inhibition of the reaction. A minimum of three concentrations were used to determine the dose-response curve and a median inhibitory concentration ($IC_{50}$).

Results—

Test compounds RIAA, curcumin, DHEA, *withania*, resveratrol, ipriflavone, astragalus, purariae radix, bonistein and parthanolide were dose dependently (20, 10, and 1 ug/ml) inhibited TNFα induced MMP-13 expression (Table 5).

Example 3

Modified Hop Extract RIAA and Herbal Extracts Dose Dependently Modulate TNFα Induced MMP-13 Expression in Human Chondrocyte Cell Line, SW1353

The Model—

The SW1353 human chondrocyte cell line model as described in Example 1.

Cell Culture and Treatment—

Standard chemicals used were described in Example 1. Following one hour of incubation with the various test compounds as listed in the table (table 3) human chondrocyte cell line, SW 1353 was stimulated with TNFα (10 ng/ml) for 24 hrs and MMP-13 were measured in the medium as described in the Example 1.

TABLE 5

Screening of test compounds for MMP-13 expression at multiple doses

| Test Compounds | ug/mL | TNFa Stimulated MMP-13 average | SD | Test Compounds | ug/mL | TNFa Stimulated MMP-13 n = 1 |
|---|---|---|---|---|---|---|
| TNF Neg | — | 0% | 1% | TNF Neg | — | 0% |
| TNF pos | | 100% | 14% | TNF pos | | 100% |
| RIAA | 20 | 45% | 6% | Berberine | 20 | −4% |
| | 10 | 74% | 5% | | 10 | −4% |
| | 5 | 94% | 2% | | 5 | −4% |
| | 1 | 120% | 7% | | 1 | −1% |
| Curcumin | 20 | −2% | 0% | THIAA | 20 | −4% |
| | 10 | −1% | 1% | | 10 | 14% |
| | 5 | 11% | 3% | | 5 | 58% |
| | 1 | 89% | 2% | | 1 | 101% |
| Bonistein | 20 | 1% | 1% | Rosemary | 20 | 8% |
| | 10 | 23% | 4% | | 10 | 33% |
| | 5 | 71% | 4% | | 5 | 55% |
| | 1 | 109% | 7% | | 1 | 93% |
| DHEA | 20 | 5% | 3% | Oleanolic acid | 20 | 26% |
| | 10 | 64% | 1% | | 10 | 43% |
| | 5 | 108% | 17% | | 5 | 38% |
| | 1 | 111% | 8% | | 1 | 95% |
| *Whithania* | 20 | 76% | 8% | Glucosamine | 20 | 105% |
| | 10 | 94% | 12% | | 10 | 107% |
| | 5 | 136% | 18% | | 5 | 137% |
| | 1 | 178% | 21% | | 1 | 126% |
| Resveratol | 20 | 45% | 12% | | | |
| | 10 | 53% | 13% | | | |
| | 5 | 88% | 11% | | | |
| | 1 | 96% | 15% | | | |
| Ipriflavone | 20 | 3% | 2% | | | |
| | 10 | 0% | 2% | | | |
| | 5 | 20% | 3% | | | |
| | 1 | 86% | 16% | | | |
| *Astragalus* | 20 | 82% | 12% | | | |
| | 10 | 88% | 14% | | | |
| | 5 | 79% | 2% | | | |
| | 1 | 92% | 13% | | | |
| *Puerariae radix* | 20 | 61% | 4% | | | |
| | 10 | 76% | 15% | | | |
| | 5 | 67% | 4% | | | |
| | 1 | 81% | 24% | | | |
| Parthenolide std | 20 | 47% | 3% | | | |
| | 10 | 72% | 3% | | | |
| | 5 | 101% | 8% | | | |
| | 1 | 119% | 1% | | | |

Determination of MMP-13 expression—The MMP-13 levels in the medium was measured as described in Example 1.

Median Effect Calculations—

Median effect calculations and inhibitory concentrations ($IC_{50}$) were performed using CalcuSyn as described in Example 2.

Results—

Test compounds RIAA, berberine sulfate, barberry stem bark (10:1), *coptis* chinensis extract (20%) and Oregon grape root extract (4:1) were dose dependently modulated TNFα induced MMP-13 expression (Table 6) in human chondrocyte cells, SW 1353.

TABLE 6

Test compounds dose dependently inhibited TNFa induced MMP-13 expression.

| Test Compounds | ug/mL | TNFa Stimulated % Activity average | SD | IC50 ug/mL |
|---|---|---|---|---|
| TNF Neg | 0 | 0% | 0% | (95% CI) |
| TNF pos |  | 100% | 7% |  |
| RIAA | 20 | 44% | 3% | 25.79 |
|  | 10 | 75% | 14% | (9.2-72.0) |
|  | 5 | 83% | 8% |  |
|  | 1 | 91% | 13% |  |
| Berberine sulfate | 1 | −1% | 0% | 0.15 |
|  | 0.5 | 4% | 2% | (0.05-0.5) |
|  | 0.1 | 50% | 6% |  |
|  | 0.05 | 99% | 13% |  |
| Barberry stem bark 10:1 | 5 | 15% | 8% | 2.00 |
|  | 2.5 | 37% | 8% | (1.6-2.5) |
|  | 1.0 | 74% | 5% |  |
|  | 0.1 | 101% | 5% |  |
| *Coptis Chinensis* extract 20% | 5 | −2% | 1% | 0.48 |
|  | 2.5 | 3% | 2% | (0.3-0.8) |
|  | 1.0 | 28% | 3% |  |
|  | 0.1 | 97% | 14% |  |
| Oregon grape root extract 4:1 | 5 | 130% | 13% |  |
|  | 2.5 | 121% | 1% |  |
|  | 1.0 | 192% | 9% |  |
|  | 0.1 | 180% | 14% |  |

Example 4

Modified Hop Extract THIAA and Berberine Sulfate Synergistically Inhibited TNFα Induced MMP-13 Expression in Human Chondrocyte Cell Line, SW1353

The Model—

The SW1353 human chondrocyte cell line was used as described in Example 1.

Materials—

All test materials were provided by Metagenics Inc (San Clemente, Calif.) All other chemicals used as described in Example 1.

Cell Culture and Treatment—

The human chondrocyte cell line, SW1353 were maintained and treatments conditions were described in Example 1. THIAA and berberine was used at various ratios (10:0; 1:10; 5:1; 2:1; 1:1; 1:2; 1:5; 1:10; 0:10) and added to the cells in medium at a final concentration of 0.1% DMSO. Following one hour of incubation with various concentrations of test compounds, TNFa (10 ng/ml) was added to the cell wells and incubation continued for 24 hours, the supernatant media was collected for MMP-13 determination.

Determination of MMP-13 expression—The MMP-13 levels in the medium was measured as described in Example 1.

Statistical Analysis and Median Effect Calculations—

Median effect calculations were performed using CalcuSyn (Biosoft, Ferguson, Mo.). This program utilizes the Median Effects Model of Chou and Talalay (Adv Enzym Regul (1984) 22:27-55) and fits the equation:

$$\log C = \beta_0 + \beta_1 \log [f_a/(1-f_c)] = 68$$

where $f_a$ is the factional inhibition of the reaction. A minimum of three concentrations were used to determine the dose-response curve and a median inhibitory concentration ($IC_{50}$).

Synergy—Combinational Index (CI) values were measured using CalcuSyn (Biosoft, Ferguson, Mo.). CI values less than 1 represent synergy and more than 1 represent non-synergy combinations (Greco, W. R., Bravo, G., and Parsons, J. C. (1995).

Results—

CI value less than 1 showed synergy. All the combinations of THIAA and berberine sulfate exhibited synergy for TNFa induced MMP-13 expression at one or more concentrations tested (Table 7A). Non synergistic combinations were highlighted. THIAA and berberine sulfate inhibited TNFα induced MMP-13 expression with IC50 of 16.424 and 0.254 ug/ml respectively (Table 7B).

TABLE 7A

Synergistic effect of THIAA and berberine TNFα induced MMP-13 expression in human chondrocyte cell line, SW1353

| CI | THIAA (ug/ml) | Berberine (ug/ml) | CI | THIAA (ug/ml) | Berberine (ug/ml) | CI | THIAA (ug/ml) | Berberine (ug/ml) | CI | THIAA (ug/ml) | Berberine (ug/ml) |
|---|---|---|---|---|---|---|---|---|---|---|---|
| 0.597 | 0.003 | 0.026 | 0.470 | 0.004 | 0.020 | 1.192 | 0.025 | 0.050 | 0.454 | 0.019 | 0.019 |
| 0.574 | 0.004 | 0.038 | 0.462 | 0.006 | 0.030 | 1.099 | 0.036 | 0.072 | 0.456 | 0.029 | 0.029 |
| 0.558 | 0.005 | 0.052 | 0.456 | 0.008 | 0.042 | 1.032 | 0.047 | 0.095 | 0.460 | 0.042 | 0.042 |
| 0.548 | 0.006 | 0.063 | 0.453 | 0.010 | 0.052 | 0.994 | 0.057 | 0.113 | 0.462 | 0.052 | 0.052 |
| 0.540 | 0.007 | 0.073 | 0.450 | 0.012 | 0.061 | 0.966 | 0.064 | 0.129 | 0.464 | 0.061 | 0.061 |
| 0.534 | 0.008 | 0.082 | 0.448 | 0.014 | 0.069 | 0.943 | 0.072 | 0.144 | 0.466 | 0.070 | 0.070 |
| 0.529 | 0.009 | 0.091 | 0.446 | 0.015 | 0.077 | 0.924 | 0.079 | 0.158 | 0.467 | 0.079 | 0.079 |
| 0.524 | 0.010 | 0.100 | 0.444 | 0.017 | 0.085 | 0.907 | 0.086 | 0.172 | 0.469 | 0.088 | 0.088 |
| 0.520 | 0.011 | 0.110 | 0.443 | 0.019 | 0.093 | 0.891 | 0.093 | 0.187 | 0.470 | 0.098 | 0.098 |
| 0.515 | 0.012 | 0.119 | 0.442 | 0.020 | 0.102 | 0.877 | 0.101 | 0.202 | 0.472 | 0.108 | 0.108 |
| 0.511 | 0.013 | 0.130 | 0.440 | 0.022 | 0.111 | 0.863 | 0.109 | 0.218 | 0.473 | 0.118 | 0.118 |
| 0.507 | 0.014 | 0.141 | 0.439 | 0.024 | 0.122 | 0.849 | 0.117 | 0.235 | 0.475 | 0.130 | 0.130 |

TABLE 7A-continued

Synergistic effect of THIAA and berberine TNFα induced MMP-13 expression in human chondrocyte cell line, SW1353

| 0.503 | 0.015 | 0.154 | 0.437 | 0.027 | 0.133 | 0.835 | 0.127 | 0.253 | 0.476 | 0.144 | 0.144 |
| 0.499 | 0.017 | 0.168 | 0.436 | 0.029 | 0.146 | 0.821 | 0.137 | 0.275 | 0.478 | 0.159 | 0.159 |
| 0.495 | 0.018 | 0.185 | 0.434 | 0.032 | 0.162 | 0.806 | 0.150 | 0.299 | 0.480 | 0.177 | 0.177 |
| 0.490 | 0.021 | 0.205 | 0.433 | 0.036 | 0.181 | 0.790 | 0.165 | 0.329 | 0.482 | 0.200 | 0.200 |
| 0.484 | 0.023 | 0.231 | 0.431 | 0.041 | 0.205 | 0.772 | 0.184 | 0.367 | 0.484 | 0.229 | 0.229 |
| 0.478 | 0.027 | 0.267 | 0.428 | 0.048 | 0.240 | 0.751 | 0.209 | 0.419 | 0.487 | 0.270 | 0.270 |
| 0.469 | 0.032 | 0.324 | 0.425 | 0.059 | 0.294 | 0.724 | 0.249 | 0.498 | 0.491 | 0.337 | 0.337 |
| 0.456 | 0.044 | 0.443 | 0.421 | 0.082 | 0.408 | 0.682 | 0.330 | 0.661 | 0.497 | 0.481 | 0.481 |
| 0.428 | 0.088 | 0.881 | 0.410 | 0.169 | 0.846 | 0.598 | 0.616 | 1.232 | 0.513 | 1.054 | 1.054 |

| | | | CI | THIAA (ug/ml) | Berberine (ug/ml) | CI | THIAA (ug/ml) | Berberine (ug/ml) | CI | THIAA (ug/ml) | Berberine (ug/ml) |
|---|---|---|---|---|---|---|---|---|---|---|---|
| | | | 0.121 | 0.009 | 0.005 | 0.675 | 0.115 | 0.023 | 0.395 | 0.111 | 0.011 |
| | | | 0.167 | 0.021 | 0.010 | 0.623 | 0.173 | 0.035 | 0.402 | 0.192 | 0.019 |
| | | | 0.217 | 0.038 | 0.019 | 0.589 | 0.238 | 0.048 | 0.413 | 0.294 | 0.029 |
| | | | 0.256 | 0.056 | 0.028 | 0.571 | 0.290 | 0.058 | 0.422 | 0.384 | 0.038 |
| | | | 0.290 | 0.075 | 0.037 | 0.559 | 0.337 | 0.067 | 0.430 | 0.469 | 0.047 |
| | | | 0.321 | 0.095 | 0.047 | 0.550 | 0.382 | 0.076 | 0.438 | 0.553 | 0.055 |
| | | | 0.351 | 0.117 | 0.058 | 0.542 | 0.425 | 0.085 | 0.445 | 0.639 | 0.064 |
| | | | 0.381 | 0.141 | 0.070 | 0.535 | 0.469 | 0.094 | 0.452 | 0.729 | 0.073 |
| | | | 0.412 | 0.168 | 0.084 | 0.529 | 0.514 | 0.103 | 0.458 | 0.824 | 0.082 |
| | | | 0.443 | 0.199 | 0.099 | 0.524 | 0.561 | 0.112 | 0.465 | 0.926 | 0.093 |
| | | | 0.477 | 0.235 | 0.117 | 0.518 | 0.611 | 0.122 | 0.472 | 1.039 | 0.104 |
| | | | 0.512 | 0.277 | 0.139 | 0.513 | 0.666 | 0.133 | 0.480 | 1.166 | 0.117 |
| | | | 0.552 | 0.328 | 0.164 | 0.508 | 0.728 | 0.146 | 0.488 | 1.312 | 0.131 |
| | | | 0.596 | 0.392 | 0.196 | 0.504 | 0.798 | 0.160 | 0.496 | 1.483 | 0.148 |
| | | | 0.648 | 0.473 | 0.237 | 0.498 | 0.880 | 0.176 | 0.506 | 1.691 | 0.169 |
| | | | 0.710 | 0.583 | 0.291 | 0.493 | 0.980 | 0.196 | 0.517 | 1.953 | 0.195 |
| | | | 0.789 | 0.739 | 0.370 | 0.487 | 1.108 | 0.222 | 0.530 | 2.304 | 0.230 |
| | | | 0.896 | 0.986 | 0.493 | 0.480 | 1.287 | 0.257 | 0.547 | 2.814 | 0.281 |
| | | | 1.061 | 1.445 | 0.723 | 0.472 | 1.570 | 0.314 | 0.572 | 3.670 | 0.367 |
| | | | 1.396 | 2.681 | 1.340 | 0.459 | 2.163 | 0.433 | 0.615 | 5.635 | 0.564 |
| | | | 2.563 | 10.497 | 5.248 | 0.434 | 4.393 | 0.879 | 0.730 | 14.536 | 1.454 |

Non-synergistic combinations are highlighted.

TABLE 7B

THIAA and berberine sulfate inhibited TNFα induced MMP-13 expression

| Drug | Dm | r |
|---|---|---|
| THIAA | 16.42401 | 0.98789 |
| Berberine sulfate | 0.25411 | 0.99815 |

Example 5

Modified Hop Extracts and Herbal Extracts Modulate sRANKL Mediated Osteoclastogenesis The Model— sRANKL mediated osteoclastogenesis as described by Rahman, M. M., et al., (Conjugated linoleic acid inhibits osteoclast differentiation of RAW264.7 cells by modulating RANKL signaling. J. Lipid Res. 47 (8): 1739-1748, 2006).

Materials—

All test compounds were provided by Metagenics Inc (San Clemente, Calif.). Test compounds were prepared in dimethyl sufoxide (DMSO) and stored at −20° C. sRANKL, (Receptor activated NF-κB ligand), was purchased from Peprotech (Rockey Hill, N.J.). TRAP activity measurement kit was purchased from Sigma Chemicals (St Louis, Mo.)

Cell Culture and Treatment—

The murine macrophage cell line, RAW 264.7 was purchased from ATCC (Manassas, Va.) and maintained in α-MEM containing 10% FBS and plated at a concentration of $1 \times 10^4$/well in 48 well culture plate (Corning, N.Y.). Next day, test compounds (10 and 5 μg/ml) were added to the cells in medium at a final concentration of 0.1% DMSO. Following overnight incubation with the test compounds, sRANKL (50 ng/ml) or medium alone was added to the cell wells. The medium was replaced after 2 days with test compounds and sRANKL and incubation was continued for 3 additional days.

Determination of TRAP (Tartrate Resistant Acid Phsophatase) Activity—

The cells were washed twice with ice cold PBS and lysed in 150 μl of 0.2% triton x-100 in PBS. TRAP activity in cell lysates was determined by using TRAP solution from the kit (Sigma 387A1 kit), according to the manufacturers instructions. A 100 μl cell lysates was added to 100 μl of TRAP solution in 96 well plate and incubated at 37° C. for 1 hr. The absorbance was measured at 555 nm using a plate reader. The protein concentration was estimated using BCA reagent (Sigma) and the final activity was normalized for equal protein.

Statistical Analysis—

Inhibition of TRAP activity was determined by comparison of the TRAP activity in the presence of with and with out test compounds in sRANKL, activated osteoclasts. A minimum of two wells were used for each concentration.

Results—

Test compounds which modulated sRANKL, mediated TRAP activity are presented in Table 8.

TABLE 8

Modulation of sRANKL mediated TRAP activity

| Test Compounds | ug/mL | % TRAP Activity average | SD | Test Compounds | ug/mL | % TRAP Activity average | SD |
|---|---|---|---|---|---|---|---|
| Control | | 0% | 0% | Black cohosh | 10 | 38% | 17% |
| RANKL | | 100% | 23% | | 5 | 45% | 1% |
| RIAA | 10 | 65% | 4% | Salvia miltiorrhiza | 10 | 87% | 7% |
| | 5 | 78% | 9% | | 5 | 69% | 4% |
| Kaprex | 10 | 22% | 3% | Red Yeast Rice | 10 | 54% | 3% |
| | 5 | 36% | 11% | | 5 | 76% | 4% |
| THIAA | 10 | 0% | 3% | Glabridin | 10 | 75% | 4% |
| | 5 | 54% | 4% | | 5 | 82% | 0% |
| Tetrex | 10 | 8% | 2% | Resveratol | 10 | 2% | 4% |
| | 5 | 46% | 2% | | 5 | 11% | 7% |
| Acacia | 10 | 64% | 7% | Abelmoschus manihot | 10 | 83% | 16% |
| | 5 | 110% | 3% | | 5 | 108% | 13% |
| Rosemary | 10 | 0% | 6% | DHA | 10 | 105% | 9% |
| | 5 | 23% | 3% | | 5 | 120% | 8% |
| Oleanolic Acid | 10 | 35% | 1% | Perilla oil | 10 | 84% | 0% |
| | 5 | 61% | 1% | | 5 | 71% | 3% |
| Curcumin | 10 | −22% | 0% | Camellia sinesis | 10 | 94% | 1% |
| | 5 | −17% | 3% | | 5 | 113% | 9% |
| Hyaluronic Acid | 10 | 2% | 5% | Green tea | 10 | 73% | 16% |
| | 5 | 35% | 17% | | 5 | 88% | 11% |
| Glucosamine | 10 | 48% | 20% | Dioscorea spogiosa | 10 | 71% | 4% |
| | 5 | 75% | 20% | | 5 | 67% | 1% |
| Green Tea Polyphenols | 10 | 79% | 11% | Quercetin | 10 | 62% | 5% |
| | 5 | 65% | 4% | | 5 | 73% | 4% |
| Punica Granatum | 10 | 240% | 33% | Hesperidin | 10 | 76% | 2% |
| | 5 | 215% | 26% | | 5 | 81% | 2% |
| Devil's Claw | 10 | 67% | 2% | Berberine | 10 | −8% | 2% |
| | 5 | 67% | 13% | | 5 | 4% | 6% |
| Parthenolide | 10 | 8% | 1% | Flax seed extract | 10 | 102% | 0% |
| | 5 | 50% | 2% | | 5 | 97% | 4% |
| MBP | 10 | 101% | 7% | Oleuropein | 10 | 81% | 1% |
| | 5 | 99% | 2% | | 5 | 82% | 10% |
| Bonepep | 10 | 89% | 3% | Olive oil | 10 | 61% | 6% |
| | 5 | 79% | 7% | | 5 | 74% | 15% |
| Bonestein | 10 | −3% | 2% | Rutin | 10 | 74% | 7% |
| | 5 | 128% | 37% | | 5 | 106% | 20% |
| Genistein | 10 | 72% | 3% | FOS | 10 | 98% | 22% |
| | 5 | 91% | 2% | | 5 | 79% | 2% |
| DHEA | 10 | 33% | 6% | Inulin | 10 | 69% | 1% |
| | 5 | 46% | 0% | | 5 | 87% | 4% |
| Fructus Ligustri | 10 | 81% | 6% | Arthred bovine | 10 | 66% | 17% |
| | 5 | 77% | 5% | | 5 | 100% | 33% |
| Phloridizin | 10 | 150% | 10% | Arthred porcine | 10 | 72% | 7% |
| | 5 | 103% | 20% | | 5 | 68% | 0% |
| Puerariae radix | 10 | 43% | 8% | | | | |
| | 5 | 49% | 11% | | | | |

Example 6

Modified Hop Extracts and Herbal Extracts Dose Dependently Modulate sRANKL Osteoclastogenesis The Model—
sRANKL mediated osteoclastogenesis as described in Example 5.

Materials—
All test compounds were provided by Metagenics Inc (San Clemente, Calif.). Purchase of other chemicals was described in Example 5.

Cell Culture and Treatment—
The maintenance of murine macrophage cell line, RAW 264.7 and cell treatment was described in Example 5. Multiple concentration of test compounds (10 and 5 μg/ml) were used to determine the effect on sRANKL induced TRAP activity.

Determination of TRAP Activity—
Determination of TRAP activity was described in Example 5.

Statistical Analysis—
Inhibition of TRAP activity was determined by comparison in the presence of with and with out test compounds in sRANKL activated osteoclasts. A minimum of two wells were used for each concentration. The basal TRAP activity levels with out sRANKL stimulation was subtracted from sRANKL stimulation to get the sRANKL induced TRAP activity and the activity was normalized to 100%. The percent activity of test compounds was measured in the presence of sRANKL and referred as sRANKL induced TRAP activity.

A minimum of three concentrations were used to determine median inhibitory concentration ($IC_{50}$). IC50 values were measured using CalcuSyn program (Biosoft, Fergusson, Mo.) as described in Example 2.

Results—
Test compounds inhibited sRANKL mediated TRAP activity as indicated in Table 9 below.

TABLE 9

Hop and herbal extracts dose dependently modulated sRANKL mediated TRAP activity.

| Test Compounds | ug/mL | % TRAP activity average | SD | Test Compounds | ug/mL | % TRAP activity average | SD |
|---|---|---|---|---|---|---|---|
| Control | 0 | 0% | 1% | *Withania somnifera* | 10 | 69% | 0% |
| RANKL | 0 | 100% | 16% |  | 5 | 87% | 9% |
|  |  |  |  |  | 1 | 120% | 0% |
| RIAA | 10 | 69% | 6% | *Puerariae radix* | 10 | 87% | 6% |
|  | 5 | 112% | 5% |  | 5 | 108% | 0% |
|  | 1 | 90% | 52% |  | 1 | 114% | 9% |
| THIAA | 10 | 4% | 3% | Black Cohosh | 10 | 103% | 14% |
|  | 5 | 65% | 4% |  | 5 | 128% | 15% |
|  | 1 | 113% | 8% |  | 1 | 154% | 2% |
| HHIAA | 10 | 22% | 15% | Resveratol | 10 | 16% | 2% |
|  | 5 | 104% | 1% |  | 5 | 17% | 30% |
|  | 1 | 120% | 16% |  | 1 | 117% | 1% |
| Rosemary | 10 | 7% | 5% | Ipriflavone | 10 | 82% | 5% |
|  | 5 | 39% | 3% |  | 5 | 164% | 34% |
|  | 1 | 117% | 10% |  | 1 | 168% | 5% |
| Oleanolic acid | 10 | 32% | 1% | Policosanol | 10 | 103% | 1% |
|  | 5 | 63% | 6% |  | 5 | 139% | 6% |
|  | 1 | 139% | 1% |  | 1 | 152% | 15% |
| *Acacia* | 10 | 91% | 17% | Berberine | 10 | 7% | 1% |
|  | 5 | 176% | 14% |  | 5 | 15% | 5% |
|  | 1 | 169% | 1% |  | 1 | 68% | 9% |
| Curcumin | 5 | −1% | 9% | Conjugated Linoleic acid | 10 | 79% | 15% |
|  | 2.5 | 46% | 25% |  | 5 | 81% | 8% |
|  | 1 | 92% | 17% |  | 1 | 86% | 1% |
| Parthenolide Std | 5 | 70% | 14% | Chicken Collagen Type II Kolla2 | 10 | 87% | 9% |
|  | 2.5 | 85% | 12% |  | 5 | 125% | 4% |
|  | 1 | 117% | 45% |  | 1 | 102% | 8% |
| Hyaluronic acid | 10 | 111% | 17% | OsteoSine | 10 | 38% | 5% |
|  | 5 | 130% | 1% |  | 5 | 53% | 1% |
|  | 1 | 122% | 4% |  | 1 | 68% | 6% |
| Glucosamine | 10 | 269% | 188% | MCHA | 10 | 105% | 17% |
|  | 5 | 183% | 13% |  | 5 | 111% | 1% |
|  | 1 | 179% | 58% |  | 1 | 105% | 1% |
| African Devil's claw | 10 | 119% | 31% | Prune (PLUM) PE | 10 | 142% | 3% |
|  | 5 | 197% | 43% |  | 5 | 141% | 11% |
|  | 1 | 153% | 19% |  | 1 | 101% | 4% |
| Parthenolide | 10 | 29% | 6% | Epimedium | 10 | 77% | 3% |
|  | 5 | 78% | 3% |  | 5 | 89% | 4% |
|  | 1 | 106% | 10% |  | 1 | 84% | 2% |
| Bonistein | 10 | 18% | 45% | Black rice | 10 | 72% | 4% |
|  | 5 | 346% | 13% |  | 5 | 20% | 0% |
|  | 1 | 184% | 1% |  | 1 | 63% | 2% |

Example 7

Clinical Effects on Pain Reduction and Flexibility of a Berberine/Tetrahydroisoalpha Acid Composition The purpose of this experiment was to determine the effects of a berberine/tetrahydroisoalpha acid composition on joint pain and flexibility in volunteers.

A small, open label, non-controlled study was conducted on 12 volunteer subjects whose clinical history and exam indicated that additional therapeutics were necessary beyond bodywork (here chiropractic manipulation). Examples included patients in whom bodywork had only been of brief help previously requiring repeated adjustments, patients with active inflammatory challenges including chronic and acute pain states, and patients with poor tissue integrity secondary to chronicity, fibrosis (fibromyalgia), and hypothyroidism.

Questionnaires were administered at baseline prior to body work and administration of two tablets prior to initial manipulation of a composition comprising 100 mg of berberine and 100 mg of tetrahydroisoalpha acids as the active moieties, and thereafter immediately following body work, and at 1 hour, 6 hours, 24 hours, and 7 days time points after body work (1-3 tablets per day). Subjects were asked to score using Likert scales of 1-10 the severity of their pain and lack of flexibility. On the pain scale, a score of 10 represented the highest level of pain. On the flexibility scale, a score of 1 represented the least level of flexibility. The results are presented in Table 10 below.

TABLE 10

Clinical effects on pain reduction and flexibility of a berberine/tetrahydroisoalpha acid composition

|  | Likert Scores | Pain | Flexibility |
|---|---|---|---|
| Averages | BEFORE Visit: | 6.67 | 4.08 |
|  | IMMEDIATELY AFTER Visit: | 2.67 | 6.58 |
|  | ~1 HOUR AFTER Visit: | 2.67 | 6.58 |
|  | ~6 HOURS AFTER Visit: | 2.92 | 6.58 |
|  | ~24 HOURS AFTER Visit: | 3.50 | 6.83 |
|  | ~7 DAYS AFTER Visit: | 3.92 |  |
| % change | BEFORE Visit. |  |  |
|  | IMMEDIATELY AFTER Visit: | −60.0% | 61.2% |
|  | ~1 HOUR AFTER Visit: | −60.0% | 61.2% |
|  | ~6 HOURS AFTER Visit: | −56.3% | 61.2% |
|  | ~24 HOURS AFTER Visit: | −47.5% | 67.3% |
|  | ~7 DAYS AFTER Visit: | −41.3% |  |

The significant reduction in pain (41-60%) and improvements in flexibility (61%-67%) and the persistence of this benefit were considered to represent a significant clinical response.

Side effects noted by 2 subjects were minimal GI discomfort after taking the product on an empty stomach. This was addressed by taking with food. One subject had more persistent GI discomfort including a presumed episode of GERD.

Three subjects were followed for 2-3 week intervals as they used the product. Moderate clinical improvement was noted by the clinician. His comments included "that with less trigger point tenderness, he was more effectively able to address the issue using body work" in one case.

The invention claimed is:

1. A method to promote bone and joint health in a mammal in need thereof, said method comprising administering to the mammal a composition comprising a therapeutically effective amount of berberine or a pharmaceutically acceptable salt thereof and a therapeutically effective amount of a substituted 1,3-cyclopentadione compound selected from the group consisting of tetrahydroisoalpha acids and pharmaceutically acceptable salts thereof, wherein the berberine and the substituted 1,3-cyclopentadione compound are in synergistic amounts and in a synergistic ratio with combination index of less than 1 for synergistic inhibition of MMP-13 expression.

2. The method of claim 1, wherein the tetrahydroisoalpha acid is selected from the group consisting of (4R,5S)-3,4-dihydroxy-2-(3-methylbutanoyl)-5-(3-methylbutyl)-4-(4-methylpentanoyl)cyclopent-2-en-1-one; (4S,5S)-3,4-dihydroxy-2-(3-methylbutanoyl)-5-(3-methylbutyl)-4-(4-methylpentanoyl)cyclopent-2-en-1-one, (4S,5R)-3,4-dihydroxy-2-(3-methylbutanoyl)-5-(3-methylbutyl)-4-(4-methylpentanoyl)cyclopent-2-en-1-one, (4R,5R)-3,4-dihydroxy-2-(3-methylbutanoyl)-5-(3-methylbutyl)-4-(4-methylpentanoyl)cyclopent-2-en-1-one, (4R,5S)-3,4-dihydroxy-5-(3-methylbutyl)-4-(4-methylpentanoyl)-2-(3-methylpropanoyl)cyclopent-2-en-1-one, (4S,5S)-3,4-dihydroxy-5-(3-methylbutyl)-4-(4-methylpentanoyl)-2-(3-methylpropanoyl)cyclopent-2-en-1-one, (4S,5R)-3,4-dihydroxy-5-(3-methylbutyl)-4-(4-methylpentanoyl)-2-(3-methylpropanoyl)cyclopent-2-en-1-one, (4S,5R)-3,4-dihydroxy-5-(3-methylbutyl)-4-(4-methylpentanoyl)-2-(3-methylpropanoyl)cyclopent-2-en-1-one, (4R,5S)-3,4-dihydroxy-2-(2-methylbutanoyl)-5-(3-methylbutyl)-4-(4-methylpentanoyl)cyclopent-2-en-1-one, (4S,5S)-3,4-dihydroxy-2-(2-methylbutanoyl)-5-(3-methylbutyl)-4-(4-methylpentanoyl)cyclopent-2-en-1-one, (4S,5R)-3,4-dihydroxy-2-(2-methylbutanoyl)-5-(3-methylbutyl)-4-(4-methylpentanoyl)cyclopent-2-en-1-one, and (4R,5R)-3,4-dihydroxy-2-(2-methylbutanoyl)-5-(3-methylbutyl)-4-(4-methylpentanoyl)cyclopent-2-en-1-one.

3. The method according to claim 1, wherein the composition further comprises a pharmaceutically acceptable excipient selected from the group consisting of coatings, isotonic and absorption delaying agents, binders, adhesives, lubricants, disintergrants, coloring agents, flavoring agents, sweetening agents, absorbants, detergents, and emulsifying agents.

4. The method according to claim 1, wherein the composition further comprises one or more members selected from the group consisting of antioxidants, vitamins, minerals, proteins, fats, and carbohydrates.

5. A composition to promote bone and joint health in a mammal in need thereof comprising a therapeutically effective amount of berberine or a pharmaceutically acceptable salt thereof and a therapeutically effective amount of a substituted 1,3-cyclopentadione compound selected from the group consisting of tetrahydroisoalpha acids and pharmaceutically acceptable salts thereof, wherein the berberine and the substituted 1,3-cyclopentadione compound are in synergistic amounts and in a synergistic ratio with combination index of less than 1 for synergistic inhibition of MMP-13 expression.

6. The composition according to claim 5, wherein the tetrahydroisoalpha acid is selected from the group consisting of (4R,5S)-3,4-dihydroxy-2-(3-methylbutanoyl)-5-(3-methylbutyl)-4-(4-methylpentanoyl)cyclopent-2-en-1-one; (4S,5S)-3,4-dihydroxy-2-(3-methylbutanoyl)-5-(3-methylbutyl)-4-(4-methylpentanoyl)cyclopent-2-en-1-one; (4S,5R)-3,4-dihydroxy-2-(3-methylbutanoyl)-5-(3-methylbutyl)-4-(4-methylpentanoyl)cyclopent-2-en-1-one; (4R,5R)-3,4-dihydroxy-2-(3-methylbutanoyl)-5-(3-methylbutyl)-4-(4-methylpentanoyl)cyclopent-2-en-1-one; (4R,5S)-3,4-dihydroxy-5-(3-methylbutyl)-4-(4-methylpentanoyl)-2-(3-methylpropanoyl)cyclopent-2-en-1-one; (4S,5S)-3,4-dihydroxy-5-(3-methylbutyl)-4-(4-methylpentanoyl)-2-(3-methylpropanoyl)cyclopent-2-en-1-one; (4S,5R)-3,4-dihydroxy-5-(3-methylbutyl)-4-(4-methylpentanoyl)-2-(3-methylpropanoyl)cyclopent-2-en-1-one; (4R,5R)-3,4-dihydroxy-5-(3-methylbutyl)-4-(4-methylpentanoyl)-2-(3-methylpropanoyl)cyclopent-2-en-1-one; (4R,5S)-3,4-dihydroxy-2-(2-methylbutanoyl)-5-(3-methylbutyl)-4-(4-methylpentanoyl)cyclopent-2-en-1-one; (4S,5S)-3,4-dihydroxy-2-(2-methylbutanoyl)-5-(3-methylbutyl)-4-(4-methylpentanoyl)cyclopent-2-en-1-one; (4S,5R)-3,4-dihydroxy-2-(2-methylbutanoyl)-5-(3-methylbutyl)-4-(4-methylpentanoyl)cyclopent-2-en-1-one; and (4R,5R)-3,4-dihydroxy-2-(2-methylbutanoyl)-5-(3-methylbutyl)-4-(4-methylpentmaoyl)cyclopent-2-en-1-one.

7. The composition according to claim 5, wherein the composition further comprises a pharmaceutically acceptable excipient selected from the group consisting of coatings, isotonic and absorption delaying agents, binders, adhesives, lubricants, disintergrants, coloring agents, flavoring agents, sweetening agents, absorbants, detergents, and emulsifying agents.

8. The composition according to claim 5, wherein the composition further comprises one or more members selected from the group consisting of antioxidants, vitamins, minerals, proteins, fats, and carbohydrates.

9. The method according to claim 1, wherein the composition comprises from about 10 mg to about 800 mg of berberine or a pharmaceutically acceptable salt thereof and from about 10 mg to about 800 mg of a tetrahydroisoalpha acid or a pharmaceutically acceptable salt thereof, wherein the tetrahydroisoalpha acid is selected from the group consisting of (4R,5R)-3,4-dihydroxy-2-(3-methylbutanoyl)-5-(3-methylbutyl)-4-(4-methylpentanoyl)cyclopent-2-en-1-one; (4S,5S)-3,4-dihydroxy-2-(3-methylbutanoyl)-5-(3-methylbutyl)-4-(4-methylpentanoyl)cyclopent-2-en-1-one, (4S,5R)-3,4-dihydroxy-2-(3-methylbutanoyl)-5-(3-methylbutyl)-4-(4-methylpentanoyl)cyclopent-2-en-1-one, (4R,5R)-3,4-dihydroxy-2-(3-methylbutanoyl)-5-(3-methylbutyl)-4-(4-methylpentanoyl)cyclopent-2-en-1-one, (4R,5S)-3,4-dihydroxy-5-(3-methylbutyl)-4-(4-methylpentanoyl)-2-(3-methylpropanoyl)cyclopent-2-en-1-one, (4S,5S)-3,4-dihydroxy-5-(3-methylbutyl)-4-(4-methylpentanoyl)-2-(3-methylpropanoyl)cyclopent-2-en-1-one, (4S,5R)-3,4-dihydroxy-5-(3-methylbutyl)-4-(4-methylpentanoyl)-2-(3-methylpropanoyl)cyclopent-2-en-1-one, (4R,5R)-3,4-dihydroxy-5-(3-methylbutyl)-4-(4-methyl pentanoyl)-2-(3-methylpropanoyl)cyclopent-2-en-1-one, (4R,5S)-3,4-dihydroxy-2-(2-methylbutanoyl)-5-(3-methylbutyl)-4-(4-methylpentanoyl)cyclopent-2-en-1-one, (4S,5S)-3,4-dihydroxy-2-(2-methylbutanoyl)-5-(3-methylbutyl)-4-(4- methylpentanoyl)cyclopent-2-en-1-one, (4S,5R)-3,4-dihydroxy-2-(2-methylbutanoyl)-5-(3-methylbutyl)-4-(4-methylpentanoyl)cyclopent-2-en-1-one, and (4R,5R)-3,4-dihydroxy-2-(2-methylbutanoyl)-5-(3-methylbutyl)-4-(4-methylpentanoyl)cyclopent-2-en-1-one.

10. The composition according to claim 5, wherein the composition comprises from 10 mg to about 800 mg of berberine or a pharmaceutically acceptable salt thereof and from about 10 mg to about 800 mg of tetrahydroisoalpha acid or a pharmaceutically acceptable salt thereof, wherein the tetrahydroisoalpha acid is selected from the group consisting of (4R,5S)-3,4-dihydroxy-2-(3-methylbutanoyl)-5-(3-methylbutyl)-4-(4-methylpentanoyl)cyclopent-2-en-1-one; (4S,5S)-3,4-dihydroxy-2-(3-methylbutanoyl)-5-(3-methylbutyl)-4-(4-methylpentanoyl)cyclopent-2-en-1-one; (4S,5R)-3,4-dihydroxy-2-(3-methylbutanoyl)-5-(3-methylbutyl)-4-(4-methylpentanoyl)cyclopent-2-en-1-one; (4R,5R)-3,4-dihydroxy-2-(3-methylbutanoyl)-5-(3-methylbutyl)-4-(4-methylpentanoyl)cyclopent-2-en-1-one; (4R,5S)-3,4-dihydroxy-5-(3-methylbutyl)-4-(4-methylpentanoyl)-2-(3-methylpropanoyl)cyclopent-2-en-1-one; (4S,5S)-3,4-dihydroxy-5-(3-methylbutyl)-4-(4-methylpentanoyl)-2-(3-methylpropanoyl)cyclopent-2-en-1-one; (4S,5R)-3,4-dihydroxy-5-(3-methylbutyl)-4-(4-methylpentanoyl)-2-(3-methylpropanoyl)cyclopent-2-en-1-one; (4R,5R)-3,4-dihydroxy-5-(3-methylbutyl)-4-(4-methylpentanoyl)-2-(3-methylpropanoyl)cyclopent-2-en-1-one; (4R,5S)-3,4-dihydroxy-2-(2-methylbutanoyl)-5-(3-methylbutyl)-4-(4-methylpentanoyl)cyclopent-2-en-1-one; (4S,5S)-3,4-dihydroxy-2-(2-methylbutanoyl)-5-(3-methylbutyl)-4-(4-methylpentanoyl)cyclopent-2-en-1-one; (4S,5R)-3,4-dihydroxy-2-(2-methylbutanoyl)-5-(3-methylbutyl)-4-(4-methylpentanoyl)cyclopent-2-en-1-one; and (4R,5R)-3,4-dihydroxy-2-(2-methylbutanoyl)-5-(3-methylbutyl)-4-(4-methylpentmaoyl)cyclopent-2-en-1-one.

* * * * *